US008591902B2

(12) United States Patent
Hirabayashi et al.

(10) Patent No.: US 8,591,902 B2
(45) Date of Patent: Nov. 26, 2013

(54) ANTIBODY BINDING TO LYSOPHOSPHATIDYLGLUCOSIDE, AND COMPOSITION COMPRISING THE SAME

(75) Inventors: Yoshio Hirabayashi, Wako (JP); Hiroyuki Kamiguchi, Wako (JP); Kunihiro Ohta, Wako (JP); Akiho Nakamura, Wako (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 13/808,475

(22) PCT Filed: Jul. 7, 2011

(86) PCT No.: PCT/JP2011/065597
§ 371 (c)(1),
(2), (4) Date: Feb. 15, 2013

(87) PCT Pub. No.: WO2012/005328
PCT Pub. Date: Jan. 12, 2012

(65) Prior Publication Data

US 2013/0142813 A1 Jun. 6, 2013

(30) Foreign Application Priority Data

Jul. 7, 2010 (JP) ................................ 2010-155278

(51) Int. Cl.
*C07K 16/18* (2006.01)
*A61K 31/7028* (2006.01)
*G01N 33/53* (2006.01)

(52) U.S. Cl.
USPC .................. 424/175.1; 530/389.8; 530/387.3; 530/388.2

(58) Field of Classification Search
None
See application file for complete search history.

(56) References Cited

FOREIGN PATENT DOCUMENTS

WO 2007069603 6/2007

OTHER PUBLICATIONS

Nagatsuka et al., Phosphatidylglucoside: A new marker for lipid rafts. Biochimica et Biophysica Acta 1780 (2008) 405-409.*
Behar et al., "Semaphorin III is needed for normal patterning and growth of nerves, bones and heart", Nature, 383:525-528 (1996).
Berghuis et al., "Hardwiring the Brain: Endocannabinoids Shape Neuronal Connectivity", Science, 316:1212-1216 (2007).
Bron et al., "Functional Knockdown of neuropilin-1 in the developing chick nervous system by siRNA hairpins phenocopies genetic ablation in the mouse", Developmental dynamics, 230:299-308 (2004).
Catalano et al., "Many major CNS axon projections develop normally in the absence of semaphorin III", Molecular and Cellular Neuroscience, 11:173-182, 1998.

(Continued)

*Primary Examiner* — Gregory S Emch
*Assistant Examiner* — Aurora M Fontainhas
(74) *Attorney, Agent, or Firm* — Sughrue Mion, PLLC

(57) ABSTRACT

In order to identify a factor demonstrating a repellent effect on axon extension of a neuron, lysophosphatidylglucoside (LPG) has been found to have an activity as a chemorepellent effect on axon guidance of a DRG sensory neuron specific to a neuron expressing TrkA, an NGF receptor.
In addition, it has been found out that suppressing the function of LPG makes it possible to suppress a repellent effect of LPG on axon extension of a neuron expressing TrkA. A molecule capable of suppressing the function of LPG can be a composition promoting repairing of a neural circuit in neuronal damages and the like.

7 Claims, 15 Drawing Sheets

A B C D

(56) References Cited

OTHER PUBLICATIONS

Contos et al., "Requirement for the $Ip_{A1}$ lysophosphatidic acid receptor gene in normal suckling behavior", Proc. Natl. Acad. Sci., USA, 97:13384-13389 (2000).
Dickson, "Molecular Mechanisms of Axon Guidance", Science, 298:1959-1964 (2002).
Estivill-Torrus et al., "Absence of LPA, Signaling Results in defective Cortical Development", Cerebral Cortex, 18:938-950 (2008).
Fu et al., "SEMA3A Regulates developing sensory projections in the chicken spinal cord", J. Neurobiology, 45:277-236 (2000).
Gu et al., "Neuropilin-1 conveys semaphorin and VEGF signaling during neural and cardiovascular development", Developmental Cell, 5:45-57 (2003).
International Search Report for PCT/JP2011/065597 dated Aug. 2, 2011, with Written Opinion.
Kamiguchi, "Axon guidance mediated by lysophosphatidylglucoside", Neuroscience Research, 65(1):S17 [#SY2-C1-3] (2009).
Kitsukawa et al., "Neuropilin-Semaphorin III/D-Mediated Chemorepulsive signals play a crucial role in peripheral nerve projection in mice", Neuron, 19:995-1005 (1997).
Luo et al., "Collapsin: a protein in brain that induces the collapse and paralysis of neuronal growth cones", Cell, 75(2):217-227 (1993).
Masuda et al., "Differential non-target-derived repulsive signals play a critical role in shaping initial axonal growth of dorsal root ganglion neurons", Developmental Biology, 254:289-302 (2003).
Masuda et al.,"Chemorepulsion and cell adhesion molecules in patterning initial trajectories of sensory axons", Neuroscience Research, 51:337-347 (2005).
Mendelson et al., "Developmental of cutaneous and proprioceptive afferent projections in the chick spinal cord", Neurosci. Letters, 138(1):72-76 (1992).
Messersmith et al., "Semaphorin III can function as a selective chemorepellant to pattern sensory projections in the spinal cord", Neuron, 14:949-959 (1995).
Nagatsuka et al., "A new phosphoglycerolipid, 'phosphatidylglucose', found in human cord red cell by multi-reactive monoclonal anti-i cold agglutinin", FEBS_Lett., 497:141-147 (2001).
Nagatsuka et al., "Carbohydrate-dependent signaling from the phosphatidylglucoside-based microdomain induces granulocytic differentiation of HL60 cells", Proc. Natl. Acad. Sci., USA, 100:7454-7459 (2003).
Nagatsuka et al., "Phosphatidylglucoside exists as a single molecule species with saturated fatty acyl chains in developing astroglial membranes", Biochemistry, 45:8742-8750 (2006).
Ozaki et al., "Initial Trajectories of sensory axons toward laminar targets in the developing mouse spinal cord", J. of Comparative Neurology, 380:215-229 (1997).
Perrin et al., "Distinct subpopulations of sensory afferents require F11 or axonin-1 for growth to their target layers within the spinal cord of the chick", Neuron, 30(3):707-723 (2001).
Pond et al., "Temporal Regulation of Neuropilin-1 Expression and Sensitivity to Semaphorin 3A in NGF- and NT3- Responsive chick sensory neurons", J. Neurobiology, 51:43-53 (2002).
Puschel et al., "Murine semaphorin D/Collapsin is a member of a diverse gene family and creates domains inhibitory for axonal extension", Neuron, 14:941-948 (1995).
Sharma et al., "Sensory axons are guided by local cues in the developing dorsal spinal cord", Development, 125:635-643 (1998).
Shepherd et al., "A sensory axon repellant secreted from ventral spinal cord explants is neutralized by antibodies raised against collapsin-1", Development, 124:1377-1385 (1997).
Short et al., "Metabolism of the Glycosyl diglycerides and phosphatidylglucose of *Staphylococcus aureus*", J. of Bacteriology, 104(1):126-132 (1970).
Snider et al., "Dorsal root ganglion neurons require functional neurotrophin receptors for survival during development", Philos. Trans. R. Soc. Lond. B. Biol. Sci., 351(1338):395-403 (1996).
Strochlic et al., "A role for S1P signaling in axon guidance in the *Xenopus* visual system", Development, 135:333-342 (2008).
Takashima et al., "Targeting of both mouse neuropilin-1 and neuropilin-2 genes severely impairs developmental yolk sac and embryonic angiogenesis", Proc. Natl. Acad. Sci., USA, 99(6):3657-3662 (2002).
Taniguchi et al., "Disruption of *Semaphorin III/D* Gene causes severe abnormality in peripheral nerve projection", Neuron, 19:519-530 (1997).
Watanabe et al., "Dorsally derived netrin-1 provides an inhibitory cue and elaborates the 'waiting period' for primary sensory axons in the developing spinal cord", Development, 133:1379-1387 (2006).
Wright et al., "The guidance molecule semaphorin III is expressed in regions of spinal cord and periphery avoided by growing sensory axons", J. Comp. Neurol., 361(2):321-333 (1995).
Yamazaki et al., "Comprehensive analysis of monoclonal antibodies against detergent-insoluble membrane/lipid rafts of HL60 cells", J. of Immunological Methods, 311:106-116 (2006).

* cited by examiner

```
                              SEQUENCE LISTING


<160> NUMBER OF SEQ ID NOS: 20

<210> SEQ ID NO 1
<211> LENGTH: 17
<212> TYPE: PRT
<213> ORGANISM: Gallus gallus
<220> FEATURE:
<221> NAME/KEY: SITE
<222> LOCATION: (1)..(17)
<223> OTHER INFORMATION: Anti LPG antibody#15  Lv CDR1

<400> SEQUENCE: 1

Ser Gly Gly Gly Ser Tyr Ala Gly Thr Tyr Tyr Tyr Gly Tyr Arg Tyr
1               5                   10                  15

Gly


<210> SEQ ID NO 2
<211> LENGTH: 7
<212> TYPE: PRT
<213> ORGANISM: Gallus gallus
<220> FEATURE:
<221> NAME/KEY: SITE
<222> LOCATION: (1)..(7)
<223> OTHER INFORMATION: Anti LPG antibody#15 Lv CDR2

<400> SEQUENCE: 2

Tyr Asn Asp Lys Arg Pro Ser
1               5


<210> SEQ ID NO 3
<211> LENGTH: 9
<212> TYPE: PRT
<213> ORGANISM: Gallus gallus
<220> FEATURE:
<221> NAME/KEY: SITE
<222> LOCATION: (1)..(9)
<223> OTHER INFORMATION: Anti LPG antibody#15 Lv CDR3

<400> SEQUENCE: 3

Gly Ser Tyr Asp Asn Ser Gly Ala Ala
1               5


<210> SEQ ID NO 4
<211> LENGTH: 5
<212> TYPE: PRT
<213> ORGANISM: Gallus gallus
<220> FEATURE:
<221> NAME/KEY: SITE
```

```
<222> LOCATION: (1)..(5)
<223> OTHER INFORMATION: Anti LPG antibody#15 Hv CDR1

<400> SEQUENCE: 4

Ser Asn Ala Met Gly
1               5


<210> SEQ ID NO 5
<211> LENGTH: 16
<212> TYPE: PRT
<213> ORGANISM: Gallus gallus
<220> FEATURE:
<221> NAME/KEY: SITE
<222> LOCATION: (1)..(16)
<223> OTHER INFORMATION: Anti LPG antibody#15 Hv CDR2

<400> SEQUENCE: 5

Gly Ile Asp Asp Asp Gly Ser Ser Thr Arg Tyr Ala Pro Ala Val Lys
1               5                   10                  15


<210> SEQ ID NO 6
<211> LENGTH: 17
<212> TYPE: PRT
<213> ORGANISM: Gallus gallus
<220> FEATURE:
<221> NAME/KEY: SITE
<222> LOCATION: (1)..(17)
<223> OTHER INFORMATION: Anti LPG antibody#15 Hv CDR3

<400> SEQUENCE: 6

Cys Ala Tyr Ser Ser Gly Cys Asp Tyr Glu Ala Gly Tyr Ile Asp Ala
1               5                   10                  15

Trp


<210> SEQ ID NO 7
<211> LENGTH: 111
<212> TYPE: PRT
<213> ORGANISM: Gallus gallus
<220> FEATURE:
<221> NAME/KEY: SITE
<222> LOCATION: (1)..(111)
<223> OTHER INFORMATION: Anti LPG antibody#15 Lv

<400> SEQUENCE: 7

Ala Val Thr Gln Pro Ala Ser Val Ser Ala Asn Pro Gly Glu Thr Val
1               5                   10                  15

Arg Ile Thr Cys Ser Gly Gly Gly Ser Tyr Ala Gly Thr Tyr Tyr Tyr
            20                  25                  30

Gly Tyr Arg Tyr Gly Trp Tyr Gln Gln Lys Ser Pro Gly Ser Ala Pro
        35                  40                  45

Val Thr Val Ile Tyr Tyr Asn Asp Lys Arg Pro Ser Asp Ile Pro Ser
    50                  55                  60

Arg Phe Ser Gly Ser Leu Ser Gly Ser Thr Asn Thr Leu Thr Ile Thr
65                  70                  75                  80

Gly Val Arg Ala Asp Asp Glu Ala Val Tyr Phe Cys Gly Ser Tyr Asp
                85                  90                  95

Asn Ser Gly Ala Ala Phe Gly Ala Gly Thr Thr Leu Thr Val Leu
            100                 105                 110


<210> SEQ ID NO 8
<211> LENGTH: 125
<212> TYPE: PRT
<213> ORGANISM: Gallus gallus
<220> FEATURE:
<221> NAME/KEY: SITE
```

<222> LOCATION: (1)..(125)
<223> OTHER INFORMATION: Anti LPG antibody#15 Hv

<400> SEQUENCE: 8

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Ser Thr Arg Tyr Ala Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Ile Tyr Tyr Cys
                85                  90                  95

Thr Lys Cys Ala Tyr Ser Ser Gly Cys Asp Tyr Glu Ala Gly Tyr Ile
            100                 105                 110

Asp Ala Trp Gly His Gly Thr Glu Val Ile Val Ser Ser
        115                 120                 125
```

<210> SEQ ID NO 9
<211> LENGTH: 347
<212> TYPE: DNA
<213> ORGANISM: Gallus gallus
<220> FEATURE:
<221> NAME/KEY: V_region
<222> LOCATION: (1)..(347)
<223> OTHER INFORMATION: Anti LPG antibody#15 Lv cDNA

<400> SEQUENCE: 9

```
agcagtgact cagccggcct cggtgtcagc aaacccagga gaaaccgtca ggatcacctg     60

ctccgggggt ggcagctatg ctggaactta ctattatggc tataggtatg gctggtatca    120

gcagaagtca cctggcagtg cccctgtcac tgtgatctat tacaacgaca agagaccctc    180

ggacatccct tcacgattct ccggttccct atccggctcc acaaacacat taaccatcac    240

tggggtccga gccgatgacg aggctgtcta tttctgtggg agctacgaca acagtggtgc    300

tgcatttggg gccgggacaa ccctgaccgt cctaggtgag tcgctga                  347
```

<210> SEQ ID NO 10
<211> LENGTH: 330
<212> TYPE: DNA
<213> ORGANISM: Gallus gallus
<220> FEATURE:
<221> NAME/KEY: V_region
<222> LOCATION: (1)..(330)
<223> OTHER INFORMATION: Anti LPG antibody#15 Hv cDNA

<400> SEQUENCE: 10

```
cgctcagcct cgtctgcaag gcctccgggt tcaccttcag cagtaacgcc atgggttggg     60

tgcgacaggc gcccggcaag gggctggagt gggtcgcggg tattgatgat gatggtagta    120

gcacaagata cgcgccggcg gtgaagggcc gtgccaccat ctcgagggac aacgggcaga    180

gcacagtgag gctgcagctg aacaacctca gggctgagga caccggcatc tactactgca    240

cgaaatgtgc ttacagtagt ggttgtgatt atgaagctgg ttatatcgac gcatggggcc    300

acgggaccga agtcatcgtc tcctccgcct                                     330
```

<210> SEQ ID NO 11
<211> LENGTH: 13

<212> TYPE: PRT
<213> ORGANISM: Gallus gallus
<220> FEATURE:
<221> NAME/KEY: SITE
<222> LOCATION: (1)..(13)
<223> OTHER INFORMATION: Anti LPG antibody#7 Lv CDR1

<400> SEQUENCE: 11

Ser Gly Gly Gly Ser Tyr Ala Gly Ser Tyr Tyr Tyr Gly
1 5 10

<210> SEQ ID NO 12
<211> LENGTH: 7
<212> TYPE: PRT
<213> ORGANISM: Gallus gallus
<220> FEATURE:
<221> NAME/KEY: SITE
<222> LOCATION: (1)..(7)
<223> OTHER INFORMATION: Anti LPG antibody#7 Lv CDR2

<400> SEQUENCE: 12

Asp Asn Thr Asn Arg Pro Ser
1 5

<210> SEQ ID NO 13
<211> LENGTH: 9
<212> TYPE: PRT
<213> ORGANISM: Gallus gallus
<220> FEATURE:
<221> NAME/KEY: SITE
<222> LOCATION: (1)..(9)
<223> OTHER INFORMATION: Anti LPG antibody#7 Lv CDR3

<400> SEQUENCE: 13

Gly Ser Ala Asp Asn Ser Gly Ala Ala
1 5

<210> SEQ ID NO 14
<211> LENGTH: 5
<212> TYPE: PRT
<213> ORGANISM: Gallus gallus
<220> FEATURE:
<221> NAME/KEY: SITE
<222> LOCATION: (1)..(5)
<223> OTHER INFORMATION: Anti LPG antibody#7 Hv CDR1

<400> SEQUENCE: 14

Ser Asn Ala Met Gly
1 5

<210> SEQ ID NO 15
<211> LENGTH: 16
<212> TYPE: PRT
<213> ORGANISM: Gallus gallus
<220> FEATURE:
<221> NAME/KEY: SITE
<222> LOCATION: (1)..(16)
<223> OTHER INFORMATION: Anti LPG antibody#7 Hv CDR2

<400> SEQUENCE: 15

Gly Ile Asp Asp Asp Gly Ser Gly Thr Arg Tyr Ala Pro Ala Val Lys
1 5 10 15

<210> SEQ ID NO 16
<211> LENGTH: 17
<212> TYPE: PRT
<213> ORGANISM: Gallus gallus
<220> FEATURE:
<221> NAME/KEY: SITE
<222> LOCATION: (1)..(17)

<223> OTHER INFORMATION: Anti LPG antibody#7 Hv CDR3

<400> SEQUENCE: 16

```
Cys Ala Tyr Ser Ser Gly Cys Asp Tyr Glu Ala Gly Tyr Ile Asp Ala
1               5                   10                  15

Trp
```

<210> SEQ ID NO 17
<211> LENGTH: 116
<212> TYPE: PRT
<213> ORGANISM: Gallus gallus
<220> FEATURE:
<221> NAME/KEY: SITE
<222> LOCATION: (1)..(116)
<223> OTHER INFORMATION: Anti LPG#7 antibody Lv

<400> SEQUENCE: 17

```
Ala Ala Leu Thr Gln Pro Ala Ser Val Ser Ala Asn Pro Gly Glu Thr
1               5                   10                  15

Val Lys Ile Thr Cys Ser Gly Gly Gly Ser Tyr Ala Gly Ser Tyr Tyr
            20                  25                  30

Tyr Gly Trp Tyr His Gly Ser Tyr Tyr Tyr Gly Trp Tyr Gln Gln Lys
        35                  40                  45

Ala Pro Gly Ser Ala Pro Val Thr Val Ile Tyr Asp Asn Thr Asn Arg
    50                  55                  60

Pro Ser Asn Ile Pro Ser Arg Phe Ser Gly Ser Leu Ser Gly Ser Thr
65                  70                  75                  80

Asn Thr Leu Thr Ile Thr Gly Val Arg Ala Glu Asp Glu Ala Val Tyr
                85                  90                  95

Phe Cys Gly Ser Ala Asp Asn Ser Gly Ala Ala Phe Gly Ala Gly Thr
            100                 105                 110

Thr Leu Thr Val
        115
```

<210> SEQ ID NO 18
<211> LENGTH: 98
<212> TYPE: PRT
<213> ORGANISM: Gallus gallus
<220> FEATURE:
<221> NAME/KEY: SITE
<222> LOCATION: (1)..(98)
<223> OTHER INFORMATION: Anti LPG antibody#7 Hv

<400> SEQUENCE: 18

```
Leu Ser Leu Val Cys Lys Ala Ser Gly Phe Thr Phe Ser Ser Asn Ala
1               5                   10                  15

Met Gly Trp Val Arg Gln Ala Pro Gly Lys Gly Leu Glu Trp Val Ala
            20                  25                  30

Gly Ile Asp Asp Asp Gly Ser Gly Thr Arg Tyr Ala Pro Ala Val Lys
        35                  40                  45

Gly Arg Ala Thr Ile Ser Arg Asp Asn Gly Gln Ser Thr Leu Arg Leu
    50                  55                  60

Gln Leu Asn Asn Leu Arg Ala Glu Asp Thr Gly Ile Tyr Tyr Cys Thr
65                  70                  75                  80

Lys Cys Ala Tyr Ser Ser Gly Cys Asp Tyr Glu Ala Gly Tyr Ile Asp
                85                  90                  95

Ala Trp
```

<210> SEQ ID NO 19
<211> LENGTH: 349

-continued

```
<212> TYPE: DNA
<213> ORGANISM: Gallus gallus
<220> FEATURE:
<221> NAME/KEY: V_region
<222> LOCATION: (1)..(349)
<223> OTHER INFORMATION: Anti LPG antibody#7 Lv cDNA

<400> SEQUENCE: 19

gcagcgctga ctcagccggc ctcggtgtca gcaaacccag gagaaaccgt caagatcacc      60

tgctccgggg gtggcagcta tgctggaagt tactattatg gctggtacca tggaagttac     120

tattatggct ggtaccagca gaaggcacct ggcagtgccc ctgtcactgt gatctatgac     180

aacaccaaca gaccctcgaa catcccttca cgattctccg gttccctatc cggctccaca     240

aacacattaa ccatcactgg ggtccgagcc gaggacgagg ctgtctattt ctgtgggagt     300

gcagacaaca gtggtgctgc atttggggcc gggacaaccc tgaccgtcc                 349


<210> SEQ ID NO 20
<211> LENGTH: 296
<212> TYPE: DNA
<213> ORGANISM: Gallus gallus
<220> FEATURE:
<221> NAME/KEY: V_region
<222> LOCATION: (1)..(296)
<223> OTHER INFORMATION: Anti LPG antibody#7 Hv cDNA

<400> SEQUENCE: 20

cgctcagcct cgtctgcaag gcctccgggt tcaccttcag cagtaacgcc atgggttggg      60

tgcgacaggc gcccggcaag gggctggagt gggtcgctgg tattgatgat gatggtagtg     120

gcacaagata cgcgccggcg gtgaagggcc gtgccaccat ctcgagggac aacgggcaga     180

gcacactgag gctgcagctg aacaacctca gggctgagga caccggcatc tactactgca     240

cgaaatgtgc ttacagtagt ggttgtgatt atgaagctgg ttatatcgac gcatgg         296
```

ANTIBODY BINDING TO LYSOPHOSPHATIDYLGLUCOSIDE, AND COMPOSITION COMPRISING THE SAME

CROSS REFERENCE TO RELATED APPLICATIONS

This application is a National Stage of International Application No. PCT/JP2011/065597 filed Jul. 7, 2011, claiming priority based on Japanese Patent Application No. 2010-155278 filed Jul. 7, 2010, the contents of all of which are incorporated herein by reference in their entirety.

TECHNICAL FIELD

The present invention relates to: an antibody being capable of binding to lysophosphatidylglucoside and having an activity of suppressing a repellent effect of lysophosphatidylglucoside on axon extension of a neuron expressing TrkA; and a composition comprising the antibody as an active ingredient.

BACKGROUND ART

In the development stage of a nerve, a dynamic structure, a so-called growth cone, is formed at a tip of an axon of the nerve as the axon extends to a target tissue. The growth cone detects signaling molecules therearound, and changes its extension direction in response to diffusible or contact-dependent guidance cues. For the detection and so forth, complex systems including organelles and receptors are utilized (NPL 1). Most of axon guidance factors identified until today are proteins and derivatives thereof. However, the researches on the lipid-based mechanism have revealed the presence of lysophosphatidic acids (NPLs 2, 3), sphingosine-1-phosphate (NPL 4), and endocannabinoids (NPL 5) as molecules playing a role in signal transduction in the brain.

As the interface between the central nerve and the peripheral nerve, accurate circuit formation in the spinal cord is important for neural development. Particularly, a connection between a dorsal root ganglion (DRG) sensory afferent axon and a spinal cord second-order neuron is a crucially important step. There are different subtypes of DRG sensory afferent nerve, which are projected into various regions in the spinal cord. All of these must enter the spinal cord via a limited region of the dorsal white matter, that is, a dorsal root entry zone (DREZ), and extend axons thereof to an appropriate target site probably while directed to a guidance cue. DRG sensory nerves with an afferent axon projected into the spinal cord are classified into two groups according to the neurotrophin receptor expression. Specifically, one is a TrkA receptor-expressing neuron dependent on NGF, a ligand of the receptor; the other is a TrkC receptor-expressing neuron dependent on NT-3, a ligand of the receptor (NPL 6). Moreover, main TrkA-expressing nerves are nociceptive, whose afferent axon terminates at the outermost layer of the dorsal horn. Meanwhile, most of TrkC-expressing nerves are proprioceptive or mechanoreceptive, whose axon is projected into a deep portion of the ventral gray matter (NPL 7).

To date, various molecular mechanisms have been identified, which control pattern formation of primary DRG afferent nerve in the spinal cord. For example, in the chicken spinal cord, axonin/TAG-1 and F11 are necessary to correctly guide nociceptive and proprioceptive afferent nerves, respectively (NPL 8). Further, in mice, a transient domain of dorsally derived netrin-1 plays an important role in controlling a timing when to enter the gray matter at an interstitial branching of collateral (NPL 9). Nevertheless, researches are most concentrated on semaphorin 3A (Sema3A). Semaphorin 3A has been identified as collapsin (factor suppressing projection extension) in the early development of avians (NPL 10), and is involved in different pattern formations of nociceptive and proprioceptive afferent nerves in the spinal cord. Specifically, it has been revealed that the former is inhibited or repelled by secreted semaphorin 3A, whereas the latter is non-responsive to the repellent (chemorepellent) signal (NPLs 11 to 15). Such a difference in chemical reactivity between the two types of nerve groups is adjusted by dynamic expression of neuropilin-1 (NRP-1), a semaphorin signal receptor. Specifically, as development proceeds, the region where Sema3A is expressed is gradually restricted to the ventral spinal cord; simultaneously, the expression of NRP-1 is increased in a nociceptive nerve. In addition, the expression of NRP-1 in proprioceptive neurons is correspondingly decreased (NPLs 15, 16).

As described above, various researches have been conducted on semaphorin 3A, and a lot of findings have been obtained. Meanwhile, the presence of a sensory nerve-guiding mechanism independent of semaphorin signal transduction in the spinal cord has been suggested for a long period of time based on in vitro and in vivo experiments (NPL 17). Tissue sections collected from the ventral spinal cord of mice homozygously deficient for Sema3A or wild type mice demonstrate a repellent effect on DRG axon extension in a coculture assay using a collagen gel (NPL 18). Moreover, in a case of in vivo, most of TrkA and TrkC nerves of Sema3A-deficient mice exhibit normal central projections into targets in ventral and dorsal gray matters (NPLs 19 to 21). Further, although an in vivo analysis cannot be conducted on a projection in the gray matter at a late stage of development because most of NRP-1-deficient mice die at embryonic day 12, the spinal cord-afferent projection is normal at least at an early stage of development (NPL 22). However, the result of a culture experiment on tissue sections collected from the ventral spinal cord of NRP-1-deficient mice confirmed a repellent effect on a DRG axon in vitro (NPL 18). Moreover, cells of double NRP-1 and Nrp-2 knockout mice are, in theory, insensitive to signal transduction by diffusible class 3 semaphorin, but die at embryonic day 8 before such an analysis can be conducted because the blood circulatory system is defective (NPL 23).

Sharma and Frank performed a microsurgical manipulation on chicken such that the ventral spinal cord of chicken was replaced with the dorsal spinal cord located opposite thereto, followed by in vitro culturing. In this event, since a sample derived from a chicken deficient in the ventral spinal cord also still had stereotypic pattern formations of proprioceptive and nociceptive afferent neurons, Sharma and Frank contest a ventral-dorsal concentration gradient mechanism of a long-range diffusible repulsive factor (NPL 24). Nonetheless, it has been revealed that before the interstitial collateral extends into the gray matter, Sema3A signal transduction plays a role in the early pattern formation of a DRG afferent nerve in DREZ in vivo. Furthermore, Gu and associates produced viable NRP-1 mutant mice by a genetic approach, and the DRG afferent nerve showed precocious interstitial extension into the dorsal horn (NPL 25). In addition, Bron and colleagues obtained a similar result by targeting SiRNA to NRP-1 in a developing spinal cord in a chicken embryo by employing in ovo electropolation. Specifically, it is known that a DRG axon "temporarily stops" the extension at a stage when the DRG axon reaches the DREZ of the spinal cord before reaching the dorsal horn. However, it was revealed that when SiRNA knocks down NRP-1, such "temporary stop (waiting period)" is shortened, and the afferent nerve prematurely enters the gray matter, extends straight as it is and reaches the midline (NPL 26). Nevertheless, such a research outcome suggests that unlike a proposed differentiation mechanism at a late stage of development, defects in the early pattern formation cause premature inward extension of TrkA and TrkC afferent nerves. Moreover, inappropriate extensions are more frequently observed in the result of the above chicken embryos than in the result of the viable knockout mice produced by Gu and colleagues. It is pointed out that this is based on a fundamental difference in guiding mechanism between rodents and avians. In mice, inward extensions of proprioceptive afferent and nociceptive afferent nerves are continuous, and the inward extension of the latter precedes that of the former by at least 24 hours. On the other hand, in chickens, both occur simultaneously. This suggests that regarding avians, the guidance cue be more important than the developmental timing to distinguish regions of the two afferent sensory nerves (NPL 27).

Meanwhile, phosphatidylglucoside (PtdGlc), one of membrane glycolipid molecules, has been identified in *Staphylococcus aureus* (NPL 28). Further, recently, similar lipids have been identified in mammalian cells as putative intercellular signal transducers (NPLs 29, 30). Then, a PtdGlc-specific monoclonal antibody (DIM2 antibody) was produced (NPL 31), and PtdGlc was identified as a marker of radial glial cells in the cortex of rat (NPL 32). It is known that PtdGlc is localized in most of the CNS (central nervous system) including the spinal cord, in addition to the cortex (NPL 32). Furthermore, lysophosphatidylglucoside is a hydrolysate of PtdGlc, and reported to demonstrate a strong repellent effect on axon extension (PTL 1). A molecule capable of suppressing the activity of a molecule having such a repellent effect, if developed, can promote repairing of a neural circuit in nervous system disorders, neurodegenerative disorders, and neuronal damages. However, such a molecule is yet to be developed.

CITATION LIST

Patent Literature

[PTL 1] International Publication No. WO2007/069603

Non Patent Literatures

[NPL 1] J. Dickson, Science 298, 1959-64 (Dec. 6, 2002).
[NPL 2] J. J. Contos, N. Fukushima, J. A. Weiner, D. Kaushal, J. Chun, Proc Natl Acad Sci USA 97, 13384-9 (Nov. 21, 2000).
[NPL 3] G. Estivill-Torrus et al., Cereb Cortex 18, 938-50 (April, 2008).
[NPL 4] L. Strochlic, A. Dwivedy, F. P. van Horck, J. Falk, C. E. Holt, Development 135, 333-42 (January, 2008).
[NPL 5] P. Berghuis et al., Science 316, 1212-6 (May 25, 2007).
[NPL 6] W. D. Snider, I. Silos-Santiago, Philos Trans R Soc Lond B Biol Sci 351, 395-403 (Mar. 29, 1996)
[NPL 7] S. Ozaki, W. D. Snider, J Comp Neurol 380, 215-29 (Apr. 7, 1997).
[NPL 8] F. E. Perrin, F. G. Rathjen, E. T. Stoeckli, Neuron 30, 707-23 (June, 2001).
[NPL 9] K. Watanabe et al., Development 133, 1379-87 (April, 2006).
[NPL 10] Y. Luo, D. Raible, J. A. Raper, *Cell* 75, 217-27 (Oct. 22, 1993).
[NPL 11] D. E. Wright, F. A. White, R. W. Gerfen, I. Silos-Santiago, W. D. Snider, J Comp Neurol 361, 321-33 (Oct. 16, 1995).
[NPL 12] E. K. Messersmith et al., Neuron 14, 949-59 (May, 1995).
[NPL 13] A. W. Puschel, R. H. Adams, H. Betz, Neuron 14, 941-8 (May, 1995).
[NPL 14] T. Shepherd, Y. Luo, F. Lefcort, L. F. Reichardt, J. A. Raper, Development 124, 1377-85 (April, 1997).
[NPL 15] S. Y. Fu, K. Sharma, Y. Luo, J. A. Raper, E. Frank, J Neurobiol 45, 227-36 (December, 2000).
[NPL 16] A. Pond, F. K. Roche, P. C. Letourneau, J Neurobiol 51, 43-53 (April, 2002).
[NPL 17] T. Masuda, T. Shiga, Neurosci Res 51, 337-47 (April, 2005).
[NPL 18] T. Masuda et al., Dev Biol 254, 289-302 (Feb. 15, 2003).
[NPL 19] 0. Behar, J. A. Golden, H. Mashimo, F. J. Schoen, M. C. Fishman, Nature 383, 525-8 (Oct. 10, 1996).
[NPL 20] M. Taniguchi et al., Neuron 19, 519-30 (September, 1997).
[NPL 21] S. M. Catalano, E. K. Messersmith, C. S. Goodman, C. J. Shatz, A. Chedotal, Mol Cell Neurosci 11, 173-82 (July, 1998).
[NPL 22] T. Kitsukawa et al., Neuron 19, 995-1005 (November, 1997).
[NPL 23] S. Takashima et al., Proc Natl Acad Sci USA 99, 3657-62 (Mar. 19, 2002).
[NPL 24] K. Sharma, E. Frank, Development 125, 635-43 (February, 1998).
[NPL 25] C. Gu et al., Dev Cell 5, 45-57 (July, 2003).
[NPL 26] R. Bron, B. J. Eickholt, M. Vermeren, N. Fragale, J. Cohen, Dev Dyn 230, 299-308 (June, 2004).
[NPL 27] B. Mendelson, H. R. Koerber, E. Frank, Neurosci Lett 138, 72-6 (Apr. 13, 1992)
[NPL 28] S. A. Short, D. C. White, J Bacterial 104, 126-32 (October, 1970).
[NPL 29] Y. Nagatsuka et al., FEBS Lett 497, 141-7 (May 25, 2001)
[NPL 30] Y. Nagatsuka et al., Proc Natl Acad Sci USA 100, 7454-9 (Jun. 24, 2003)
[NPL 31] Y. Yamazaki et al., J Immunol Methods 311, 106-16 (Apr. 20, 2006).
[NPL 32] Y. Nagatsuka et al., Biochemistry 45, 8742-50 (Jul. 25, 2006).

SUMMARY OF INVENTION

Technical Problem

The present invention has been made in view of such an awaited solution. An object of the present invention is to provide a molecule capable of suppressing a repellent effect of lysophosphatidylglucoside on axon extension of a neuron. Another object of the present invention is to provide a composition for suppressing a repellent effect of lysophosphatidylglucoside on axon extension of a neuron, the composition comprising such a molecule as an active ingredient.

Solution to Problem

In order to achieve the above objects, the present inventors first specifically analyzed the functions of PtdGlc and lysophosphatidylglucoside (Lyso-PtdGlc), a hydrolysate of PtdGlc. As a result, the inventors have revealed that: (1) in the early pattern formation of a sensory afferent nerve in the spinal cord, the lipids PtdGlc and Lyso-PtdGlc are present, (2) PtdGlc is dynamically and widely distributed into early neuroepithelial cells, white matter, and dorsal midline as the spinal cord is developed; however, PtdGlc is not present at all in a dorsal root entry zone of the spinal cord during the development of the spinal cord, (3) in in vitro experiments (an experiment using one isolated neuron, and an explant-culturing experiment in a 3D collagen gel matrix), Lyso-PtdGlc has an activity as a chemorepellent (chemorepulsant) on axon guidance of a dorsal root ganglion (DRG) sensory neuron specific to a neuron expressing TrkA, an NGF receptor (dependent on NGF), and (4) when the central nerve of an adult mouse or rat is damaged, PtdGlc expression at the damaged site is enhanced.

Hence, the present inventors next produced a monoclonal antibody specific to Lyso-PtdGlc (LPG), a hydrolysate of PtdGlc, and examined the influence on the repellent effect of Lyso-PtdGlc on a neuron expressing TrkA. Asa result, it was found out that the antibody thus produced caused abnormal axon projection of a neuron expressing TrkA in vivo (for example, abnormal projection of a DRG axon into the spinal cord gray matter, or ectopic axon deployment of a TrkA-expressing neuron into the dorsal white matter where normally a neuron expressing TrkC preferentially exists).

From these findings, the present inventors have supposed that damage to a neuron causes Lyso-PtdGlc to diffuse into an axon extension region, and the Lyso-PtdGlc may impair the subsequent axon extension. Hence, the present inventors have found out that utilization of an antibody capable of suppressing the function of Lyso-PtdGlc makes it possible to suppress a repellent effect of Lyso-PtdGlc on axon extension of a neuron expressing TrkA, and that the antibody is usable for promoting repairing of a neural circuit in nervous system disorders, neurodegenerative disorders, and neuronal damages. These discoveries have led to the completion of the present invention.

The present invention more specifically provides the following inventions.

(1) An antibody being capable of binding to lysophosphatidylglucoside, and having an activity of suppressing a repellent effect of lysophosphatidylglucoside on axon extension of a neuron expressing TrkA.

(2) An antibody comprising:

a light chain variable region including amino acid sequences of SEQ ID NOs: 1 to 3 or the amino acid sequences in at least any one of which one or more amino acids are substituted, deleted, added, and/or inserted; and a heavy chain variable region including amino acid sequences of SEQ ID NOs: 4 to 6 or the amino acid sequences in at least any one of which one or more amino acids are substituted, deleted, added, and/or inserted.

(3) An antibody comprising:

a light chain variable region including an amino acid sequence of SEQ ID NO: 7 or the amino acid sequence in which one or more amino acids are substituted, deleted, added, and/or inserted; and a heavy chain variable region including an amino acid sequence of SEQ ID NO: 8 or the amino acid sequence in which one or more amino acids are substituted, deleted, added, and/or inserted.

(4) An antibody comprising:

a light chain variable region including amino acid sequences of SEQ ID NOs: 11 to 13 or the amino acid sequences in at least any one of which one or more amino acids are substituted, deleted, added, and/or inserted; and a heavy chain variable region including amino acid sequences of SEQ ID NOs: 14 to 16 or the amino acid sequences in at least any one of which one or more amino acids are substituted, deleted, added, and/or inserted.

(5) An antibody comprising:

a light chain variable region including an amino acid sequence of SEQ ID NO: 17 or the amino acid sequence in which one or more amino acids are substituted, deleted, added, and/or inserted; and a heavy chain variable region including an amino acid sequence of SEQ ID NO: 18 or the amino acid sequence in which one or more amino acids are substituted, deleted, added, and/or inserted.

(6) An antibody produced by a hybridoma specified under any one of deposit numbers NITE P-939 and NITE P-940.

(7) An antibody capable of binding to an epitope to which the antibody according to any one of (1) to (6) binds.

(8) A composition for suppressing a repulsive action of lysophosphatidylglucoside on axon extension of a neuron expressing TrkA, the composition comprising the antibody according to anyone of (1) to (7) as an active ingredient.

(9) The composition according to (8), which is a pharmaceutical composition.

(10) The composition according to (9), which is used for promoting repairing of a neural circuit in any one of nervous system disorders, neurodegenerative disorders, and neuronal damages.

(11) A method for extending an axon of a neuron expressing TrkA, the method comprising using the antibody according to any one of (1) to (7) to suppress a repellent effect of lysophosphatidylglucoside.

(12) A method for treating any one of nervous system disorders, neurodegenerative disorders, and neuronal damages, the method comprising administering the antibody according to any one of (1) to (7).

Advantageous Effects of Invention

The present invention provides: an antibody capable of suppressing a repellent effect of Lyso-PtdGlc on axon extension of a neuron; and a composition for suppressing a repellent effect of Lyso-PtdGlc on axon extension of a neuron, the composition comprising the antibody as an active ingredient. The antibody and the composition of the present invention are capable of promoting repairing of a neural circuit in nervous system disorders, neurodegenerative disorders, and neuronal damages associated with damage to the spinal cord and/or peripheral nerve.

DESCRIPTION OF EMBODIMENTS

Figure 1:
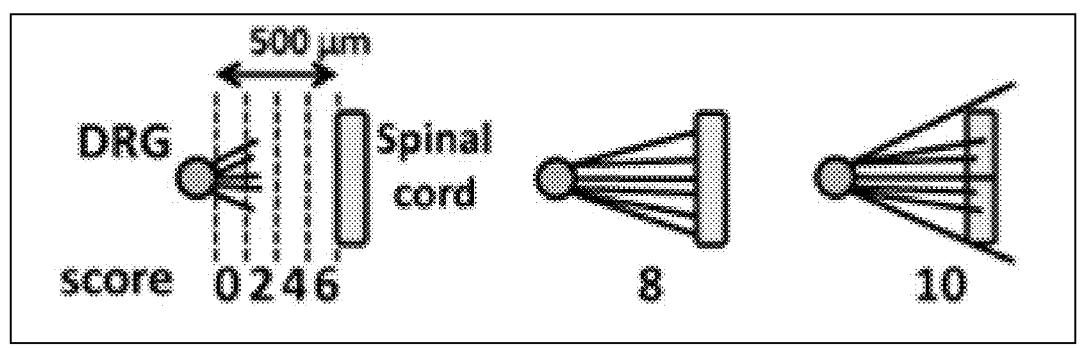
FIG. 1 is an explanatory drawing for illustrating evaluation criteria in a DRG-spinal explant coculture assay.

The present invention provides an antibody being capable of binding to lysophosphatidylglucoside, and having an activity of suppressing a repellent effect of lysophosphatidylglucoside on axon extension of a neuron expressing TrkA.

In the present invention, the "antibody" includes all classes and subclasses of immunoglobulins. The "antibody" includes a polyclonal antibody and a monoclonal antibody, and is also meant to include the form of a functional fragment of an antibody. A "polyclonal antibody" is an antibody preparation including different antibodies against different epitopes. Meanwhile, a "monoclonal antibody" means an antibody (including an antibody fragment) obtained from a substantially homogeneous antibody population. In contrast to a polyclonal antibody, a monoclonal antibody recognizes a single determinant on an antigen. The antibody of the present invention is preferably a monoclonal antibody. The antibody of the present invention is an antibody separated and/or recovered (i.e., isolated) from components in a natural environment.

In the present invention, "PtdGlc" (Phosphatidylglucoside, phosphatidyl-β-glucoside) is a compound having the following chemical structural formula.

[Chem. 1]

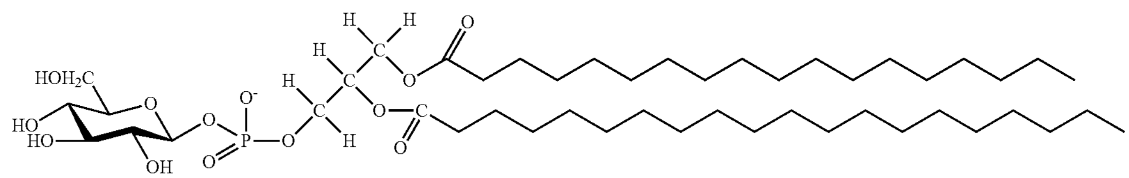

Moreover, in the present invention, "lysophosphatidylglucoside," a hydrolysate of PtdGlc, is also called Lysophosphatidylglucoside, Lyso-PtdGlc, or LPG, and is a compound having the following chemical structural formula.

[Chem. 2]

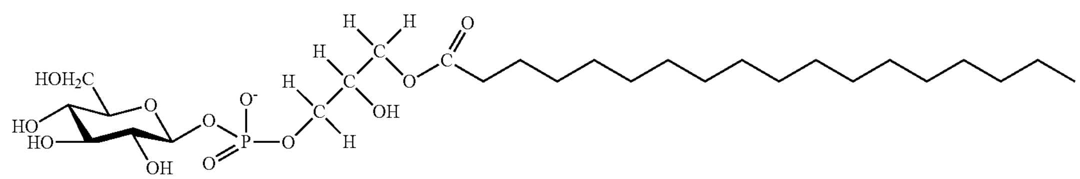

Further, "TrkA" (Tropomyosin-related kinase A), a cell membrane receptor of nerve growth factor (NGF), is a protein or a gene also called NTRK1 (NEUROTROPHIC TYROSINE KINASE RECEPTOR TYPE 1). Typically, human TrkA is a protein (gene) specified under ACCESSION No. NP_002520.2 (NM_002529.3), mouse TrkA is a protein (gene) specified under ACCESSION No. NP_001028296.1 (NM_001033124), rat TrkA is a protein (gene) specified under ACCESSION No. NP_067600.1 (NM_021589.1), and chicken TrkA is a protein (gene) specified under ACCESSION No. NP_990709.1 (NM_205378.1). Nevertheless, the protein sequences and the DNA sequences of genes encoding the proteins may be mutated naturally (i.e., non-artificially). Thus, the present invention also includes such naturally-occurring mutants.

In the present invention, the "nervous system disorders and neurodegenerative disorders" mean disorders associated with damage to the spinal cord and/or peripheral nerve. Examples thereof include traumatic neuronal damages, traumatic neurodegenerative disorders, stroke neuropathy, facial nerve paralysis, diabetic neuropathy, amyotrophic lateral sclerosis, senile dementia, Alzheimer's disease, Parkinson's disease, dysosmia, glaucoma, retinitis pigmentosa, muscular hypoplastic lateral sclerosis, amyotrophic lateral sclerosis, Huntington's disease, stroke, and the like.

Moreover, in the present invention, the "neuronal damages" mean damage to the spinal cord and/or peripheral nerve caused by not only internal factors such as diseases but also external factors such as physical compression and impact.

In the present invention, the phrase "activity of suppressing a repellent effect of lysophosphatidylglucoside on axon extension of a neuron expressing TrkA" is meant to include both in vitro and in vivo activities. The in vitro activity can be evaluated as an activity of, for example, suppressing the chemorepellent effect of Lyso-PtdGlc on extension of a neuron expressing TrkA, the chemorepellent effect detected by an in vitro turning assay described in Example 7 in the presence of a test antibody. Moreover, the in vivo activity can be evaluated as an activity of, for example, causing abnormal axon projection of a neuron expressing TrkA (for example, abnormal projection of a DRG axon into the spinal cord gray matter, or ectopic axon deployment of a TrkA-expressing neuron into the dorsal white matter where normally a neuron expressing TrkC exists preferentially) as a result of injecting a test antibody into the spinal cord in an embryo of an experimental animal as described in Example 8.

The present invention includes antibodies described in the present Examples (antibodies produced by a hybridoma specified under any one of deposit numbers NITE P-939 and NITE P-940).

A preferable embodiment of the antibody of the present invention is: an antibody comprising a light chain variable region including light chain CDR1 to CDR3 and a heavy chain variable region including heavy chain CDR1 to CDR3 of the above antibodies; or amino acid sequence mutants thereof.

The antibody comprising a light chain variable region including light chain CDR1 to CDR3 and a heavy chain variable region including heavy chain CDR1 to CDR3 of the antibody produced by the hybridoma specified under NITE P-940, and amino acid sequence mutants thereof are specifically an antibody comprising:

a light chain variable region including amino acid sequences of SEQ ID NOs: 1 to 3 or the amino acid sequences in at least any one of which one or more amino acids are substituted, deleted, added, and/or inserted; and a heavy chain variable region including amino acid sequences of SEQ ID NOs: 4 to 6 or the amino acid sequences in at least any one of which one or more amino acids are substituted, deleted, added, and/or inserted.

In addition, the antibody comprising a light chain variable region including light chain CDR1 to CDR3 and a heavy chain variable region including heavy chain CDR1 to CDR3 of the antibody produced by the hybridoma specified under NITE P-939, and amino acid sequence mutants thereof are specifically an antibody comprising:

a light chain variable region including amino acid sequences of SEQ ID NOs: 11 to 13 or the amino acid sequences in at least any one of which one or more amino acids are substituted, deleted, added, and/or inserted; and a heavy chain variable region including amino acid sequences of SEQ ID NOs: 14 to 16 or the amino acid sequences in at least any one of which one or more amino acids are substituted, deleted, added, and/or inserted.

Another preferable embodiment of the antibody of the present invention is: an antibody comprising: a light chain variable region and a heavy chain variable region of the antibodies described in the present Examples; or amino acid sequence mutants thereof. Specifically, these are an antibody comprising:

a light chain variable region including an amino acid sequence of SEQ ID NO: 7 or the amino acid sequence in which one or more amino acids are substituted, deleted, added, and/or inserted; and a heavy chain variable region including an amino acid sequence of SEQ ID NO: 8 or the amino acid sequence in which one or more amino acids are substituted, deleted, added, and/or inserted, and an antibody comprising:

a light chain variable region including an amino acid sequence of SEQ ID NO: 17 or the amino acid sequence in which one or more amino acids are substituted, deleted, added, and/or inserted; and a heavy chain variable region including an amino acid sequence of SEQ ID NO: 18 or the amino acid sequence in which one or more amino acids are substituted, deleted, added, and/or inserted. Note that the DNA sequence of a gene encoding the amino acid sequence of SEQ ID NO: 7 is shown in SEQ ID NO: 9, the DNA sequence of a gene encoding the amino acid sequence of SEQ ID NO: 8 is shown in SEQ ID NO: 10, the DNA sequence of a gene encoding the amino acid sequence of SEQ ID NO: 17 is shown in SEQ ID NO: 19, and the DNA sequence of a gene encoding the amino acid sequence of SEQ ID NO: 18 is shown in SEQ ID NO: 20.

The antibody of the present invention includes a chimeric antibody, a humanized antibody, a human antibody, and functional fragments of these antibodies. For administration as a medicine to human, the antibody of the present invention is desirably a chimeric antibody, a humanized antibody, or a human antibody from the viewpoint of side effect reduction.

In the present invention, a "chimeric antibody" is an antibody obtained by linking a variable region of an antibody of one species to a constant region of an antibody of another species. A chimeric antibody can be obtained as follows, for example. Specifically, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector. The expression vector is introduced into a host for the production of a chimeric antibody (for example, Japanese Unexamined Patent Application Publication No. Hei 7-194384, Japanese Patent No. 3238049, U.S. Pat. No. 4,816,397, U.S. Pat. No. 4,816,567, U.S. Pat. No. 5,807,715). Moreover, in the present invention, a "humanized antibody" is an antibody obtained by grafting (CDR grafting) a gene sequence of an antigen-binding site (CDR) of a non-human-derived antibody onto a human antibody gene. The preparation methods are known (see, for example, Japanese Patent No. 2912618, Japanese Patent No. 2828340, Japanese Patent No. 3068507, European Patent No. 239400, European Patent No. 125023, International Publication No. WO90/07861, International Publication No. WO96/02576). In the present invention, a "human antibody" is an antibody, all regions of which are derived from human. In preparing a human antibody, it is possible to utilize a transgenic animal (for example, a mouse) capable of producing a repertoire of the human antibody by immunization. Preparation methods of a human antibody are known (for example, Nature, 362:255-258 (1992), Intern. Rev. Immunol, 13: 65-93 (1995), J. Mol. Biol, 222: 581-597 (1991), Nature Genetics, 15: 146-156 (1997), Proc. Natl. Acad. Sci. USA, 97: 722-727 (2000), Japanese Unexamined Patent Application Publication No. Hei 10-146194, Japanese Unexamined Patent Application Publication No. Hei 10-155492, Japanese Patent No. 2938569, Japanese Unexamined Patent Application Publication No. Hei 11-206387, International Application Japanese-Phase Publication No. Hei 8-509612, International Application Japanese-Phase Publication No. Hei 11-505107).

In the present invention, a "functional fragment" of an antibody means a part (partial fragment) of an antibody, which specifically recognizes lysophosphatidylglucoside. Specific examples thereof include Fab, Fab', F(ab')2, a variable region fragment (Fv), a disulfide bonded Fv, a single chain Fv (scFv), a sc(Fv)2, a diabody, a polyspecific antibody, polymers thereof, and the like.

Here, "Fab" means a monovalent antigen-binding fragment, of an immunoglobulin, composed of a part of one light chain and a part of one heavy chain. Fab can be obtained by papain-digestion of an antibody or by a recombinant method. "Fab'" differs from Fab in that a small number of residues are added to the carboxy terminus of a heavy chain CH1 domain including one or more cysteines from an antibody hinge region. "F(ab')2" means a bivalent antigen-binding fragment, of an immunoglobulin, composed of parts of both light chains and parts of both heavy chains.

A "variable region fragment (Fv)" is a smallest antibody fragment having complete antigen recognition and binding sites. An Fv is a dimer in which a heavy chain variable region and a light chain variable region are strongly linked by non-covalent bonding. A "single chain Fv (sFv)" includes a heavy chain variable region and a light chain variable region of an antibody, and these regions exist in a single polypeptide chain. A "sc(Fv)2" is a single chain obtained by linking two heavy chain variable regions and two light chain variable regions with a linker or the like. A "diabody" is a small antibody fragment having two antigen-binding sites. The fragment includes a heavy chain variable region linked to a light chain variable region in a single polypeptide chain. Each region forms a pair with a complementary region in another chain. A "polyspecific antibody" is a monoclonal antibody having a binding specificity to at least two different antigens. For example, a polyspecific antibody can be prepared by coexpression of two immunoglobulin heavy chain/light chain pairs in which two heavy chains have different specificities.

The antibody of the present invention includes antibodies whose amino acid sequences are modified without impairing desirable activities (for example, activity of binding to lysophosphatidylglucoside, activity of suppressing a repellent effect of lysophosphatidylglucoside on axon extension of a neuron expressing TrkA). An amino acid sequence mutant of the antibody of the present invention can be prepared by introduction of a mutation into a DNA encoding an antibody chain of the present invention or by peptide synthesis. Examples of such a modification include substitution, deletion, addition, and/or insertion of a residue in the amino acid sequence of the antibody of the present invention. A site where the amino acid sequence of the antibody is modified may be a constant region of a heavy chain or a light chain of the antibody or a variable region (framework region and CDR) thereof, as long as the resulting antibody has activities equivalent to those before the modification. It is conceivable that modification on an amino acid other than those in CDR has relatively small influence on binding affinity for an antigen. As of now, there are known screening methods for antibodies whose affinity for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008)).

The number of amino acids modified is preferably 10 amino acids or less, more preferably 5 amino acids or less, and most preferably 3 amino acids or less (for example, 2 amino acids or less, or 1 amino acid). The amino acid modification is preferably conservative substitution. In the present invention, the "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), sulfur-containing amino acids (cysteine, methionine), amino acids having an amide group (asparagine, glutamine), an amino acid having an imino group (proline), and amino acids having an aromatic group (phenylalanine, tyrosine, tryptophan).

In addition, the modification on the antibody of the present invention may be a modification on post-translational process of the antibody, for example, the change in the number of sites of glycosylation or in location or type of the glycosylation. Glycosylation of an antibody is typically N-linked or O-linked glycosylation. The glycosylation of an antibody greatly depends on a host cell used for expression of the antibody. The glycosylation pattern can be modified by known methods such as introduction or deletion of a certain enzyme involved in carbohydrate production (Japanese Unexamined Patent Application Publication No. 2008-113663, Japanese Patent No. 4368530, Japanese Patent No. 4290423, U.S. Pat. No. 5,047,335, U.S. Pat. No. 5,510,261, U.S. Pat. No. 5,278,299, International Publication No. WO99/54342). Further, in the present invention, for the purpose of increasing the stability of an antibody or other purposes, an amino acid subjected to deamidation or an amino acid adjacent to the amino acid subjected to the deamidation may be substituted with a different amino acid to suppress the deamidation. Moreover, the stability of an antibody can also be increased by substituting glutamic acid with a different amino acid. The present invention also provides an antibody thus stabilized.

When the antibody of the present invention is a polyclonal antibody, the polyclonal antibody can be obtained as follows. Specifically, an animal to be immunized is immunized with an antigen (lysophosphatidylglucoside). The polyclonal antibody can be obtained by purification of an antiserum from the animal by conventional means (for example, salting-out, centrifugation, dialysis, column chromatography, or the like). Meanwhile, a monoclonal antibody can be prepared by a hybridoma method, a recombinant DNA method, or an ADLib method.

A typical example of the hybridoma method is a method by Kohler and Milstein (Kohler & Milstein, Nature, 256: 495 (1975)). Antibody-producing cells used in cell fusion process of this method are spleen cells, lymph node cells, peripheral blood leukocytes, and the like of an animal (for example, mouse, rat, hamster, rabbit, monkey, goat) immunized with an antigen (lysophosphatidylglucoside). It is also possible to use antibody-producing cells obtained by causing the antigen to act, in a medium, on the above-described types of cells, lymphocytes, or the like, which are isolated from non-immunized animals in advance. As myeloma cells, known various cell lines can be used. The antibody-producing cells and the myeloma cells may be ones originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces a monoclonal antibody specific to lysophosphatidylglucoside can be obtained. The monoclonal antibody against lysophosphatidylglucoside can be obtained by culturing the hybridoma, or from the ascites of a mammal to which the hybridoma is administered.

The recombinant DNA method is a method by which the antibody of the present invention is produced as a recombinant antibody as follows. A DNA encoding the antibody of the present invention or a peptide thereof is cloned from a hybridoma, B cells, or the like. The cloned DNA is incorporated into an appropriate vector, which is introduced into host cells (for example, a mammalian cell line, *Escherichia coli*, yeast cells, insect cells, plant cells, or the like) for the production (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding a heavy chain and a light chain may be incorporated into expression vectors, respectively to transform the host cells. Alternatively, DNAs encoding a heavy chain and a light chain may be incorporated into a single expression vector to transform the host cells (see WO94/11523). The antibody of the present invention can be obtained in a substantially pure and homogeneous form by culturing the host cells, followed by separation and purification from the host cells or the culture solution. For the separation and purification of the antibody, normal methods used for polypeptide purification can be employed. When a transgenic animal (cattle, goat, sheep, pig, or the like) incorporating an antibody gene is produced using a transgenic animal production technique, a large amount of monoclonal antibodies derived from the antibody gene can also be obtained from milk of the transgenic animal.

The ADLib method is a method as follows. Specifically, using lysophosphatidylglucoside conjugated to magnetic beads as an antigen, B-cell clones presenting on the surface an antibody having an affinity for the antigen are selected from a library of chicken B-cells constituted of DT40 cells diversified by a trichostatin A treatment (Autonomously Diversifying Library, ADLib). The B-cell clones are allowed to proliferate after limiting dilution, and monoclonal antibodies are thus obtained from the culture supernatant of such B-cell clones (Seo H. et al. Nat. Biotechnol. 23, 731-735 (2005), and Seo H. et al. Nat. Protocols. 1, 1502-1506 (2006)). Note that lysophosphatidylglucoside the antibody of the present invention recognizes is a glycolipid molecule conserved among species. Accordingly, the ADLib method free of immune tolerance can be used particularly suitably as a method for producing the antibody of the present invention.

The present invention also provides: a DNA encoding the antibody of the present invention; a vector comprising the DNA; host cells comprising the DNA; and a method for producing the antibody, comprising culturing the host cells and recovering the antibody.

Additionally, the antibody of the present invention is capable of suppressing a repellent effect of lysophosphatidylglucoside on axon extension of a neuron expressing TrkA as described in Examples later. Thus, the present invention can also provide a method for extending an axon of a neuron expressing TrkA, the method comprising using the antibody of the present invention to suppress a repellent effect of lysophosphatidylglucoside.

As an example of the method for extending an axon of the present invention, there is a method for an in vitro experimental system as described in Examples 6 and 7 later in which the antibody of the present invention is added to a culture system (collagen gel or the like) with a neuron expressing TrkA and lysophosphatidylglucoside. Meanwhile, for an in vivo experimental system as described in Example 8 later, there is a method in which the antibody of the present invention is injected by microinjection, syringe, or the like to a tissue where a neuron expressing TrkA exists or to a site where an axon of the cell extends (or a site where the extension is expected). Further, as described next, an axon of a neuron expressing TrkA can be extended by selecting a suitable form of a composition for addition or administration (injection or the like) to favorably suppress a repellent effect of lysophosphatidylglucoside.

The present invention also provides a composition for suppressing a repellent effect of lysophosphatidylglucoside on axon extension of a neuron expressing TrkA, the composition comprising the antibody of the present invention as an active ingredient. The composition of the present invention may be in the form of a pharmaceutical composition, a food, or a drink (including an animal feed) used for suppressing a repellent effect of lysophosphatidylglucoside on axon extension of a neuron expressing TrkA in vivo, or may be in the form of a reagent used for suppressing a repellent effect of lysophosphatidylglucoside on axon extension of a neuron expressing TrkA for a research purpose (for example, in vitro or in vivo experiment). When used as a pharmaceutical composition, the composition of the present invention can be used for promoting repairing of a neural circuit in, for example, nervous system disorders, neurodegenerative disorders, and neuronal damages. The present invention also provides: a pharmaceutical composition used for promoting repairing of a neural circuit in any one of nervous system disorders, neurodegenerative disorders, and neuronal damages, the composition comprising the antibody of the present invention as an active ingredient; and a method for promoting repairing of a neural circuit in any one of nervous system disorders, neurodegenerative disorders, and neuronal damages, the method comprising the step of administering an effective amount of the antibody of the present invention to a mammal including a human. The composition of the present invention is applicable to, other than human, various mammals including, for example, dogs, cats, cattle, horses, sheep, pigs, goats, rabbits, and so forth.

The composition of the present invention can be formulated by known formulation methods in pharmaceutics. The composition of the present invention can be used orally or parenterally in the form of, for example, a capsule, a tablet, a pill, a liquid, a powder, a granule, a fine granule, a film coating agent, a pellet, a troche, a sublingual tablet, a masticatory, a buccal, a paste, a syrup, a suspension, an elixir, an emulsion, an endermic liniment, an ointment, a plaster, a poultice, a percutaneous absorption preparation, a lotion, an inhalation, an aerosol, an injection, a suppository, or the like.

When formulated, these can be combined as appropriate with a carrier acceptable pharmacologically or as a food or drink, specifically, sterile water, a saline, a vegetable oil, a solvent, a base, an emulsifier, a suspension, a surfactant, a stabilizer, a flavor, an aromatic substance, an excipient, a vehicle, an antiseptic, a binder, a diluent, an isotonic agent, a soothing agent, a filler, a distintegrator, a buffer, a coating agent, a lubricant, a colorant, a sweetener, a viscous agent, a corrigent, a solubilizer, or other additives.

When used as a pharmaceutical composition, the composition of the present invention may be used in combination with another substance having a neuroregenerative action or another substance having a neural circuit-repair action. Examples of such another substance having a neuroregenerative action include neuroregeneration promoting factors such as chondroitinase ABC, cAMP, α-integrin, neurotrophine-3, NGF (Neuron Growth Factor), BDNF, and Noggin. Further, examples of another substance having a neural circuit-repair action include antagonists (for example, antibodies, low molecular weight compounds, siRNAs, shRNAs, miRNAs, ribozymes, DNAzymes, and the like) to axon extension-repellent factors such as chondroitin sulfate proteoglycans, NG2, ephrins, EphB2, Slit, Tenascin-R, semaphorin 3A, Nogo-A, and MAG. Moreover, as such combinational use, a single pharmaceutical composition containing the antibody of the present invention and at least one of another substance having a neuroregenerative action and another substance having a neural circuit-repair action may be administered; alternatively, the antibody of the present invention and at least one of another substance having a neuroregenerative action and another substance having a neural circuit-repair action may be prepared separately and administered simultaneously or at a certain interval. A suitable component ratio in the combination of the antibody of the present invention and at least one of another substance having a neuroregenerative action and another substance having a neural circuit-repair action can be selected as appropriate.

When the composition of the present invention is used as a food or drink, the food and drink may be, for example, a health food, a functional food, a food for specified health use, a nutritional supplementary food, a medical food for the ill, a food additive, or an animal feed. The food and drink of the present invention can be taken as the composition as described above, or can also be taken as various foods and drinks. In the present invention, the food and drink can be produced by production techniques known in this technical field. To the food and drink, a component or two or more components effective in nerve regeneration or neural circuit repairing may be added. Further, the food and drink of the present invention may be a multifunctional food which is a combination with another component or another functional food that demonstrates a function other than nerve regeneration or the like.

When the composition of the present invention is administered or taken, the amount administered or taken is selected as appropriate in accordance with the age, weight, symptom, and health state of the target, the type of the composition (such as drug, food, or drink), and so forth. As an example, the amount of the composition of the present invention administered or taken at one time is generally 0.01 mg/kg body weight to 100 mg/kg body weight.

A product (drug, food, reagent) of the composition of the present invention or a protocol thereof may be labelled to indicate that the use is to repair a neural circuit. Herein, the phrase "a product or a protocol is labelled" means that the body of the product, a container or a package therefor, or the like is labelled, or that a protocol, an attachment document, an advertisement, other prints, or the like disclosing information on the product is labelled. The label indicating that the use is to repair a neural circuit may include information on a mechanism of repairing a neural circuit by administering or taking the composition of the present invention. An example of the information on the mechanism is information on suppressing a repellent effect of lysophosphatidylglucoside on axon extension of a neuron expressing TrkA. Moreover, the label indicating that the use is for neuroregeneration may include information that the use is to treat or prevent nervous system disorders, neurodegenerative disorders, or neuronal damages.

Note that, it is also conceivable that the present invention is applied to treatment of nervous system disorders, neurodegenerative disorders, or neuronal damages by administered the antibody of the present invention. Thus, the present invention can also provide a method for treating any one of nervous system disorders, neurodegenerative disorders, and neuronal damages, the method comprising administering the antibody of the present invention. It is also conceivable that the pharmaceutical composition of the present invention is applicable also to diagnosis of nervous system disorders, neurodegenerative disorders, or neuronal damages.

When the antibody of the present invention is used as a diagnostic agent or used as a reagent for a research purpose, the antibody of the present invention may be labelled. As such a label, it is possible to use, for example, a radioactive substance, a fluorescent dye, a chemiluminescent substance, an enzyme, or a coenzyme. Specific examples thereof include radioisotopes, fluoresceins, rhodamines, dansyl chloride, luciferases, peroxidases, alkaline phosphatases, lysozymes, biotin/avidin, and the like. When the antibody of the present invention is to be prepared as a drug, it can be obtained in any dosage form by adopting any means suitable for the purpose. For example, a purified antibody is measured for the antibody titer and appropriately diluted with PBS (phosphate buffer containing saline) or the like; thereafter, a 0.1% sodium azide or the like can be added as an antiseptic thereto. Alternatively, for example, the antibody of the present invention adsorbed to latex or the like is determined for the antibody titer and appropriately diluted, and an antiseptic can be added thereto for use.

EXAMPLES

Hereinafter, the present invention will be described more specifically based on Examples. However, the present invention is not limited to the following Examples.

Note that in the description of the present Examples, each of the following terms means the term in the bracket. E (Embryonic day), DRG (Dorsal root ganglion), DREZ (Dorsal Root Entry Zone), HH St. (Hamburger and Hamilton Stage), LPA (Lysophosphatidic acid), LSCM (Laser scanning confocal microscopy), Lyso-PtdGlc (Lysophosphatidylglucoside), LPC (Lysophosphatidylcholine, LysoPtdCho), NGF (Nerve growth factor), NRP-1 (neuropilin-1), NT-3 (Neurotrophin-3), PtdGlc (Phosphatidyl-β-D-glucoside), Sema3A (semaphorin 3A), TLC (thin-layer chromatography), TrkA (Tropomyosin-related kinase A), TrkC (Tropomyosin-related kinase C), v/v (volume/volume).

In addition, the experiments and the analyses in Examples were carried out as follow.

(Experimental Animal)

Fertilized chicken eggs of Leghorn breed were purchased from a local producer (INOUE POULTRY FARM, Sagamihara) and kept in a shaking egg incubator (forced shaft, shakable) at 38° C. all the time until embryos developed at appropriate time. Moreover, the embryos were staged according to the Hamburger-Hamilton stages of normal chicken development (see Hamburger, V. and Hamilton, H. L., J. Morphol. 8, 49-92 (1951)). Further, all the methods and the experiments were conducted in compliance with the animal welfare guideline of Riken, Japan.

(Monoclonal Antibodies and Tissue Specimens)

Using an anti-chicken TrkA monoclonal antibody (see Oakley R A et al., J Neurosci 17: 4262-4274 (1997)) or an anti-TrkC monoclonal antibody (see Lefcort. F et al., J. Neuroscience. 16 (11) 3704-3713 (1996)), and a DIM21 monoclonal antibody (see Greimel, M. et al. Bioorg Med Chem 16, 7210-7 (Aug. 1, 2008) and NPL 31), double immunofluorescence staining was conducted on the frozen sections. The chicken embryos were separated from the eggshell at appropriate time and decapitated. The resulting body was immediately immersed into 4% (v/v) paraformaldehyde/PBS, followed by fixation at 4° C. overnight. After washing with PBS twice, the embryos were transferred into a 30% sucrose solution (4° C.) and immersed therein until each embryo was precipitated to the bottom of the solution (normally precipitated within several hours). Then, the embryo was embedded in Tissue-Tek OCT™ Compound (manufactured by Sakura Finetek Japan Co., Ltd.) and subsequently immersed into liquid nitrogen and immediately frozen. The obtained frozen block was stored at −80° C. until needed. Further, a portion of the lumbosacral spinal cord was cut out using HM560 Cryostat (manufactured by Zeiss), and the body was made into a transverse section 25 μm in thickness and stored at −20° C. until needed.

(Immunostaining)

The transverse section (slide) and so forth were returned to room temperature, and a water-repellent circle was formed on the tissue section using a wax barrier pen (manufactured by Daido Industries). In order to reduce non-specific binding of the antibodies, the section was incubated in 10% v/v normal horse serum/PBS for 1 hour. Subsequently to a blocking treatment with a serum, the primary antibody diluted with 10% serum (the dilution ratio of DIM21 was 1:500, and the dilution ratio of anti-TrkA or anti-TrkC was 1:1000) was added to the section, and incubated at 4° C. overnight. Further, before 3-hour incubation with a fluorescent dye-conjugated secondary antibody, the section labelled with the primary antibody was washed with PBS three times. Note that the secondary antibody used was anti-IgM or IgG (manufactured by Molecular Probes) conjugated with species-specific Alexa Fluor 488 or Alexa Fluor 594, and had been diluted with a serum at 1:500. After the section was stained with the secondary antibody, the section stained with the secondary antibody was washed with PBS three times and mounted. Thereafter, the antibody label binding to the section was observed with a fixed stage confocal microscope (manufactured by Olympus Corporation) and photographed using a Hamamatsu Orca camera under the control of Fluoview software.

(Spinal Cord Glia Primary Culture and Mass Spectrometry)

Spinal cord glial cells were isolated and cultured as described in T. Yoshida, M. Takeuchi, Cytotechnology 7, 187-96 (November, 1991) and S. Kentroti, A. Vernadakis, J Neurosci Res 47, 322-31 (Feb. 1, 1997). Specifically, the head of an embryo at HH St. 35 was removed, and the body was dissected. Subsequently to the ventral laminectomy, the spinal cord was isolated from the embryo, and then a membranes and a spinal nerve roots attached thereto were further removed using surgical scissors under a micros cope. The spinal cord thus obtained by isolation was suspended in a 10% FBS-containing DMEM/F12 medium, and passed through a 70-μm cell strainer using a plastic cell scraper. The resulting cell suspension was seeded onto a 10-cm cell culture dish pretreated with Poly-D-Lysine overnight, and cultured in a 10% FBS-containing DMEM/F12 medium under conditions of 37° C. and 5% $CO_2$. After culturing for 48 hours, the cultured cells were re-seeded on a fresh lysine-coated dish to remove undesirable objects, and cultured under the same conditions as described above for 120 hours or longer while replacing the medium twice. Further, some of the cells were cultured on a lysine-coated 35-mm glass cover slip for immunostaining analysis. In addition, while the medium was replaced, the culture supernatant was collected for mass spectrometry, and frozen at −80° C. and stored. Then, after culturing for 168 hours, trypsin treatment was performed, and the cells were collected from the 10-cm dish. Subsequently, in order to analyze the PtdGlc expression and glial marker by immunostaining, the cells cultured on the cover slip were treated with 4% paraformaldehyde/PBS at 4° C. overnight for fixation. Meanwhile, an ODS column (OroSep C18, 600 mg, OROCHEM CRC 18600) pretreated with methanol was filled with the collected culture supernatant of the glial cells, and a non-adsorbed fraction was washed away with pure water. Then, a substance adsorbed to the ODS column was eluted therefrom using a chloroform/methanol ($CHCl_3$/$CH_3OH$=2:1 (v/v)) mixture solution. The lipid having been adsorbed to the ODS column was dried under nitrogen gas flow, re-dissolved in 4:1 $CHCl_3$/$CH_3OH$, and filled into an iatrobead column (manufactured by Mitsubishi Kagaku Iatron, Inc.) having been equilibrated with a mixture solution of the same composition. Subsequently, elution was carried out using $CHCl_3$/$CH_3OH$ mixture solutions (4:1, 3:1, 2:1, 1:1, and 1:2) stepwise, and finally 100% $CH_3OH$. PtdGlc was eluted into a $CHCl_3$/$CH_3OH$ (2:1 and 1:1) fraction, while Lyso-PtdGlc was eluted into a $CHCl_3$/$CH_3OH$ (1:1 and 1:2) fraction. Further, to analyze the PtdGlc derived from the glial cells, the collected cells were washed with Hanks' balanced salt solution (HBSS), followed by lyophilization. The lipid was extracted with a 2:1 $CHCl_3$/$CH_3OH$ mixture solution and a $CHCl_3$/$CH_3OH$/water mixture solution (5:8:3, v/v/v), and evaporated under nitrogen gas flow. PtdGlc was extracted through an iatrobead column as the supernatant by the same method as above.

(Immunohistochemical Analysis on Primarily Cultured Spinal Glial Cells)

Before incubation in 10% normal horse serum/PBS for 1 hour and a blocking treatment with a serum, the aforementioned fixed glial cells were washed with PBS twice. A 10% serum-diluted primary antibody, either a DIM21 antibody (dilution ratio of 1:500), an EAP-3 antibody (anti-transitin antibody, dilution ratio of 1:200), or an anti-GFAP antibody (dilution ratio of 1:200, catalog number: MAB3042, manufactured by CHEMICON International, Inc.), was added to the cells and incubated at 4° C. overnight, followed by washing with PBS three times at room temperature. Further, a fluorescent dye-conjugated secondary antibody (Alexa 488-conjugated goat-derived anti-mouse IgM or Alexa 594-conjugated goat-derived anti-mouse IgM) diluted with 10% serum at 1:200 was added to the cells labelled with the primary antibody, and incubated at room temperature for 1 hour. After washing with PBS three times, the nuclei of the glial cells were labelled according to the protocol of Hoechst 33528 (manufactured by Nacalai Tesque, Inc.). The cells thus immunostained were mounted in Mowiol 4-88 solution (manufactured by Calbiochem) and stored at 4° C. The cells were observed through a 40×, oil immersion objective lens of a fixed stage confocal microscope (manufactured by Olympus Corporation), and photographed using a Hamamatsu Orca camera under the control of Fluoview software.

(Preparation of DRG Neurons for Use in Growth Cone Turning Assay)

The method described in T. Tojima et al., Nat Neurosci 10, 58-66 (January, 2007) was somewhat modified and employed to perform a primary culture of isolated DRG sensory nerves. Specifically, a chicken embryo at HH St. 29 was separated from the eggshell and decapitated. The body was transferred to ice-cooled PBS. Organs were removed from the obtained body with forceps, and the spine was exposed by ventral laminectomy. DRGs were isolated from the thoracic or lumbosacral spinal cord, broken into pieces fine watchmaker's forceps, and transferred into an L15 medium on ice. The DRG obtained by the dissection was treated with trypsin at 37° C. for 20 minutes, followed by centrifugation at 100 g for 1 minute. A minimum amount of an L15 medium was added to the pellets thus obtained, and the cells were manually suspended (repeated manual trituration). The cell suspension was again centrifuged at 100 g for 1 minute, and the supernatant was removed. Subsequently, the pellets were resuspended in a Leibovitz's L15 medium supplemented with N-2 (manufactured by Invitrogen Corp.), 750 μg/ml of BSA (manufactured by GIBCO), and 25 ng/ml of NGF or 50 ng/ml of NT-3 (manufactured by Sigma-Aldrich Corporation). The cells were seeded on glass dishes precoated with mouse-derived laminin (manufactured by Invitrogen Corp.) at 9 μg/$cm^3$ such that the cell count would be 10,000 per dish. The dishes were placed in a culturing environment of 5% $CO_2$ at 37° C. for approximately 2 hours before used in a growth cone turning assay.

(Growth Cone Turning Assay)

The in vitro growth cone turning assay was conducted according to the methods described in M. Lohof, M. Quillan, Y. Dan, M. M. Poo, J Neurosci 12, 1253-61 (April, 1992), J. Q. Zheng, M. M. Poo, J. A. Connor, Perspect Dev Neurobiol 4, 205-13 (1996), and Y. Xiang et al., Nat Neurosci 5, 843-8 (September, 2002), which were somewhat modified. Specifically, lysophosphatidylcholine (manufactured by Sigma-Aldrich Corporation) or Lyso-PtdGlc prepared by a method described later was diluted with a vehicle (1% (v/v) methanol/PBS) such that the concentration would be 10 μM. Before used in the turning assay, ultrasound was applied to the lysophospholipid or a control solution using an ultrasonic bath (manufactured by Iwaki) for 10 minutes, and the temperature was maintained at 37° C. using a warm bath. NGF (manufactured by Promega KK) and semaphorin 3A/Fc recombinant chimeric protein (manufactured by R&D SYSTEMS, INC.) were respectively used as chemoattractive and chemorepulsive positive controls, and accordingly diluted with PBS to concentrations of 50 μg/ml and 25 μg/ml before use. Further, a pipette used in the growth cone turning assay was prepared as follows. A borosilicate capillary tube (1.0 mm O. D., standard wall with filament, manufactured by Sutter Instrument Company) was pulled with Flaming-Brown P-97 micropipette puller to prepare a pipette with a long taper and a tip approximately 10 μm in aperture. The micropipette was checked with a microforge (MF-900, manufactured by Narishige Co., Ltd.) before use. The pipette was inserted into a pipette holder (manufactured by Warner Instruments), which was set above a culture dish in such a manner that the angle between the dish and the pipette would be approximately 45 degrees. The pipette was connected to a nitrogen gas cylinder, and gas discharge was controlled by an electric stimulator (manufactured by NIHON KOHDEN CORPORATION) and PV820 Picopump (manufactured by World Precision Instruments, Inc.). Note that PV820 Picopump was set to continue to discharge gas for 20 ms at intervals of 500 ms by the electric stimulator. Before the concentration gradient of the lysophospholipid was to be increased, a photograph of a candidate growth cone subjected to the experiment was taken. The system was left standing for 10 minutes. Note that a growth cone photographed using a Qimaging Qicam CCD camera under the control of Metavue software. After that, a growth cone extending straight at least 10 μm was selected as one used in this assay. The pipette tip was set at a position below a culture dish at an angle of 45 degrees to an axon extension direction and apart from the growth cone by 100 μm. Then, the electric stimulator is turned on, and the agent concentration gradient was increased. After the experiment was finished (t=45 minutes), the growth cone was photographed, the angle to the extension direction was measured by the Metavue software. Note that a growth cone not extended, a disrupted growth cone, and a growth cone having an axon branched during the period of 45 minutes were excluded from the measurement target in the present Examples. Additionally, in order to measure the turning angle of a growth cone, a straight line passing through the center of a C domain of an axon growth cone 10 minutes before an agent was added and through the center at the time of adding the agent was set to be an initial trajectory of the extension. Further, a shift from the initial trajectory after the experiment was finished was measured as the turning angle. Moreover, when an experiment was finished (t=45 minutes), a distance between the center of the C domain of the axon growth cone at the time of adding the agent (t=0) and the center at the time when the experiment was finished (t=45 minutes) was measured as the length of the axon extension.

(Explant Coculture Assay Using Collagen Gel)

A DRG-spinal explant coculture assay was conducted according to the method described in R. Keynes et al., Neuron 18, 889-97 (June, 1997). Specifically, an embryo at HH St. 35 was separated from the eggshell and decapitated. DRG and a spinal cord were isolated from the embryo and kept in an L15 medium on ice. The spinal cord having a diameter of approximately 250 μm and the dorsomedial or dorsal DRG were planted into a collagen matrix while being apart from each other by 500 μm, and cultured at 37° C. and 5% $CO_2$ for 48 hours in a DMEM/F12 medium supplemented with N2, 20 ng/ml of NGF or 50 ng/ml of NT-3, 750 μg/ml of BSA. After the culturing for 48 hours, the cultured tissue was fixed with 4% PFA at 4° C. overnight. To visualize axon extension from the DRG explant, the cultured tissue was stained with an anti-β tubulin antibody (manufactured by Chemicon). Specifically, after washing with PBS twice, the cultured tissue was incubated in 2% normal horse serum/PBS/0.1% Triton for 1 hour to reduce non-specific binding of the antibody. Then, the cultured tissue was incubated with the anti-β tubulin monoclonal antibody (diluted with 2% serum/PBS at 1:500) for 1 hour. After 15-minute washing with PBS three times, cultured tissue was incubated for 30 minutes with an Alexa 594-conjugated anti-mouse IgM antibody (manufactured by Molecular Probes) diluted 2% serum with at 1:200. After 15-minute washing with PBS three times, the cultured tissue thus stained was observed with a fixed stage confocal microscope (manufactured by Olympus Corporation), and the image was incorporated using a Hamamatsu cooled CCD camera under the control of Fluoview software. The chemorepulsive action was evaluated according to the method described in R. Keynes et al., Neuron 18, 889-97 (June, 1997). In the microscope image of the immunostained cultured tissue, the distance of 500 μm between the spinal cord and the DRG was divided by 4 (125 μm), and the length of the axon extension from the DRG explant to the spinal explant was measured for evaluation of 0 to 10 according to the following criteria.

0: The axon did not extend from DRG explant to the spinal cord explant.

2: Axon from one or more DRG explants extended to ¼ (125 μm).

4: Axon extended to 2/4 (125 μm-250 μm).

6: Axon extended to 250 μm-375 μm.

8: Axon extended and came into contact with the spinal cord.

10: Axon extended and not only came into contact with the spinal cord, but also passed over or under the spinal cord, so that the axon extended beyond the spinal cord explant (see FIG. 1).

As described above, all of the cultured tissues were evaluated according to the 0 to 10 scale: one having had the strongest chemorepulsive action was evaluated as 0, while one having had the weakest was evaluated as 10.

(Microinjection into Spinal Cord in Embryo and DiI Iontophoresis)

The methods described in E. T. Stoeckli, L. T. Landmesser, Neuron 14, 1165-79 (June, 1995) and F. E. Perrin, F. G. Rathjen, E. T. Stoeckli, Neuron 30, 707-23 (June, 2001) were somewhat modified and employed to micro-inject a specific monoclonal antibody having a function inhibitory activity into the central canal of the embryonic spinal cord during development. At incubation day 3 (E3), the shell was pierced with 18 ga needle, which was inserted to a blunt end side of the egg, so that 2 to 3 ml of the egg white was extracted. Then, a hole (window) of 4 to 5 $cm^2$ was opened at an upper portion of the eggshell with scissors. The hole was sealed with a glass cover slip, which was fixed with a fusable paraffin wax. Subsequently, the egg with the hole was incubated without shaking until HH St. 23 (normally, the development stage reaches approximately 24 hours after the egg perforation). Later-described anti-Lyso-PtdGlc or control IgM was injected into the spinal cord by 1 mg/ml four times every 8 hours. Note that 0.05% Fast Green had been added to the antibody solution so that the quality and the quantity of the injection were able to be evaluated under a microscope immediately. Moreover, as a visible mark, all the injections were performed on the spinal cord right in the middle of the hindlimbs. At the time of the injection, the egg was transferred from the egg incubator to a stereoscopic dissecting microscope (manufactured by Nikon Corporation). The cover slip was removed, and the antibody was injected. After the injection, the cover slip was returned and sealed with a wax again, and the egg was returned to the egg incubator. After the last antibody was injected, the embryo was allowed to grow (recovered) in the egg incubator approximately for 24 hours until HH St. 28. After the recovery period was completed, the embryo was removed from the eggshell and decapitated. The body was fixed overnight using 4% v/v PFA/PBS at 4° C. Then, the fixed specimen was washed with PBS, and embedded in 15% gelatin (manufactured by Sigma-Aldrich Corporation). The body was cut out using a Leica VT1000S vibratome, and a 250-μm thick horizontal section of the lumbosacral spinal cord was obtained. The DRG sensory afferent nerve was labelled with a lipid-affinity dye DiI (1,1'-dioctadecyl-3,3,3'3'-tetramethylindocarbocyanine perchlorate, FastDiI, manufactured by Molecular Probes) introduced by the iontophoresis. DiI was prepared to have a concentration of 5 mg/ml with a mixture solution of ethanol and dimethylformamide (1:1), with which a glass microelectrode (manufactured by Sutter Instrument Company) was backfilled. The electrode loaded with DiI was filled with 3 μl of 100% ethanol and next with 3 μl of 2 M lithium chloride from the back, and was connected to a 12-V power source. Then, by targeting the tip of the microelectrode to dorsomedial DRG, the TrkA nerve was specifically labelled. After the labelling, the tissue section was stored at room temperature in dark for 2 to 7 days to diffuse the dye. After the storage period was completed, the labelled section was observed with LSCM (z series 8-12 confocal section, step size: 3 μm). Specifically, the labelled section was observed through a dry objective lens (magnification: 20× or 40×) of a fixed stage confocal microscope (manufactured by Olympus Corporation) under the control of Fluoview software, and photographed using a Hamamatsu Orca CCD camera.

(Statistical Analysis)

The statistical analysis was conducted using a GraphPad Prism 4 program (for Macintosh, ver. 4.0b, manufactured by GraphPad Software, Inc.).

Example 1

Figure 2:
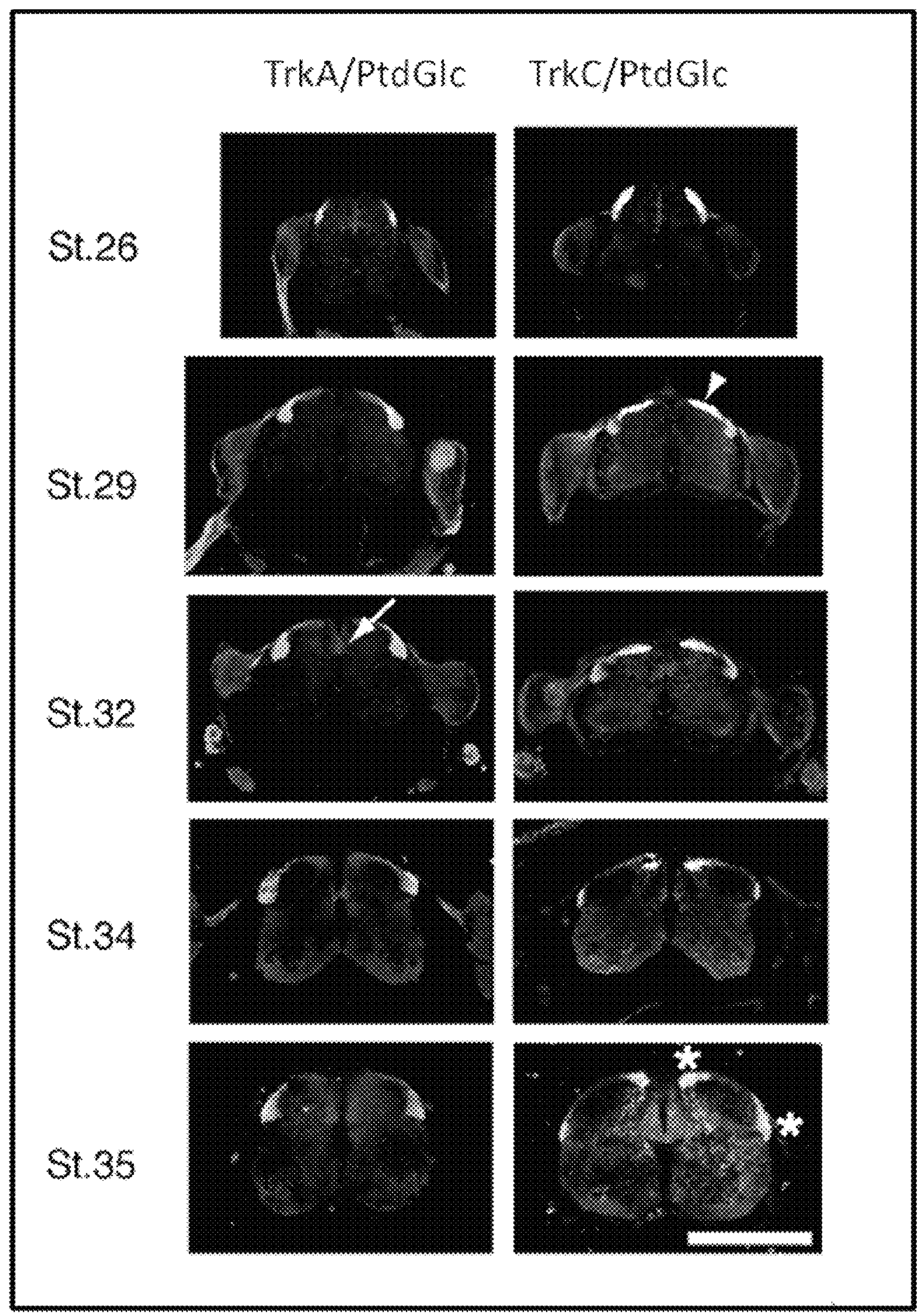
FIG. 2 shows microscope images for illustrating the result of analyzing the spinal cords of chicken embryos at HH Sts. 26, 29, 32, 34, and 35 by a co-immunostaining method using an anti-TrkA antibody or an anti-TrkC antibody, and an anti-PtdGlc antibody.

To observe spatial and temporal relations between phosphatidyl-β-D-glucoside (PtdGlc) and DRG sensory neuronal cells in the spinal cord, co-immunostaining (labelling) was performed on embryos at HH Sts. 26, 29, 32, 34, and 35 (corresponding to embryos between approximately E5 (embryonic day 5) to E9 (embryonic day 9)) using the anti-TrkA antibody or the anti-TrkC antibody, and the DIM21 antibody. FIG. 2 shows the obtained result. Note that the white line in FIG. 2 is a scale bar, representing a length of 500 μm. Moreover, in FIG. 2, a portion emitting magenta fluorescence indicates a site stained with the DIM21 antibody, a portion emitting green fluorescence indicates a site stained with the anti-TrkA antibody (left lanes in FIG. 2) or the anti-TrkC antibody (right lanes in FIG. 2).

As apparent from the result shown in FIG. 2, in the embryonic spinal cord at HH St. 26, a site having a strong immunoreactivity to DIM21 is restricted to the dorsal white matter, while a weak site is restricted to a lateral white matter located immediately behind the oval bundle of His. The expression was also observed in progenitor cells (neuroepithelial cells) in the dorsal grey matter and the dorsal midline as a punctuate staining pattern. At this stage, the TrkA-expressing region in the spinal cord was restricted to the oval bundle of His, serving as a boundary of between DIM21 antigen expressing sites on the dorsal side and the ventral side in the white matter. It was observed that TrkC was also expressed in the oval bundle of His, but localized also in the white matter of the primordial dorsal funiculus where PtdGlc abundantly existed.

In the embryonic spinal cord at HH St. 29, the immunoreactivity to PtdGlc was reduced in the dorsal grey matter, but quite strongly expressed in the primordial dorsal funiculus. The expression was weakly observed on the ventral side of DREZ and in the lateral white matter. Moreover, the TrkA-expressing region was restricted to DREZ Meanwhile, TrkC was also quite strongly expressed in this region, and furthermore in the dorsal white matter, that is, indicated by the arrowhead (triangle) in FIG. 2. The strong expression was also observed at the site where PtdGlc was strongly expressed.

In the embryonic spinal cord at HH St. 32, PtdGlc was localized in the dorsal white matter. Moreover, PtdGlc expression was also observed on both sides of the dorsomedial midline (the sites are indicated by the arrow in FIG. 2) and PtdGlc diffused toward the gray matter therefrom. Furthermore, at this stage, PtdGlc expression was also observed strongly in the lateral and ventral white matters. On the other hand, it was observed that the TrkA-expressing region was restricted to DREZ and the outermost layer of the dorsal horn. Meanwhile, the TrkC-expressing region was also DREZ and the outermost layer of the dorsal horn. In addition to these, TrkC expression was also observed in the dorsal white matter.

In the embryonic spinal cord at HH St. 34, PtdGlc was strongly expressed in the dorsomedial and ventral white matters. Further, the expression was also observed strongly in the gray matter on both sides of the dorsal midline. Moreover, the TrkA-expressing region was restricted to DREZ and the outermost layer of the dorsal horn. It was that observed that this region was still clearly distinguished from the PtdGlc-expressing region. Meanwhile, TrkC was strongly expressed in DREZ and the dorsomedial white matter. The coexistence with PtdGlc was observed in these regions.

In the embryonic spinal cord at HH St. 35, PtdGlc expression was observed strongly in three regions: the center of the ventral white matter including the primordial dorsal funiculus, the central portion of the gray matter on the dorsal side of the central canal, and the ventral and dorsal white matters. Meanwhile, at this stage, TrkA expression was restricted to DREZ and the outermost layer of the dorsal horn, a complementary relation to the PtdGlc-expressing region was observed. Moreover, TrkC was strongly expressed in DREZ and the dorsomedial white matter, and observed together with the PtdGlc expression in some regions (sites indicated by the asterisks in FIG. 2). Further, TrkC expression was also observed in the central portion of the gray matter (site of the ventral horn where a TrkC-expressing axon collateral extended toward a motor nucleus).

Additionally, although unillustrated, PtdGlc expression was promptly reduced in the embryonic spinal cord after HH St. 35. It was observed that the expression was no longer detected by HH St. 38 (approximately E12 (embryonic day 12)).

In this manner, there were regions where TrkC and PtdGlc expressed together in the early development of the spinal cord. In contrast, the boundary between TrkA and PtdGlc clearly existed at any stage. This boundary suggests that PtdGlc or a derivative thereof functions as a signaling molecule influencing two types of DRG sensory nerve (TrkC-expressing neuron and TrkA-expressing neuron) differently, in other words, acting as a chemorepulsant specifically to a TrkA-expressing neuron.

Example 2

Figure 3:
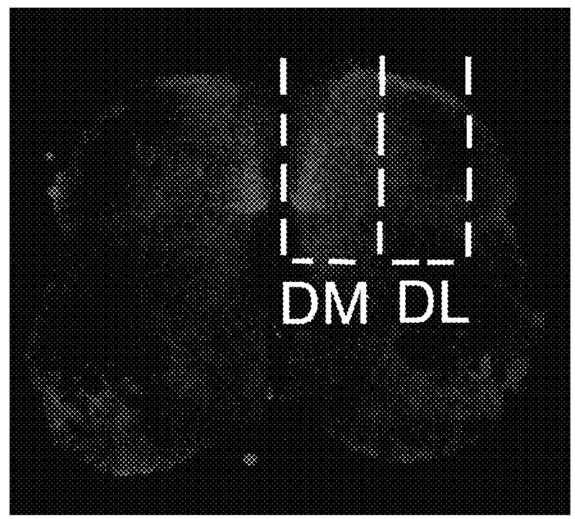
FIG. 3 shows a microscope image for illustrating the result of analyzing an explant from the spinal cord of a chicken embryo by an immunostaining method using an anti-PtdGlc antibody.
Figure 4:
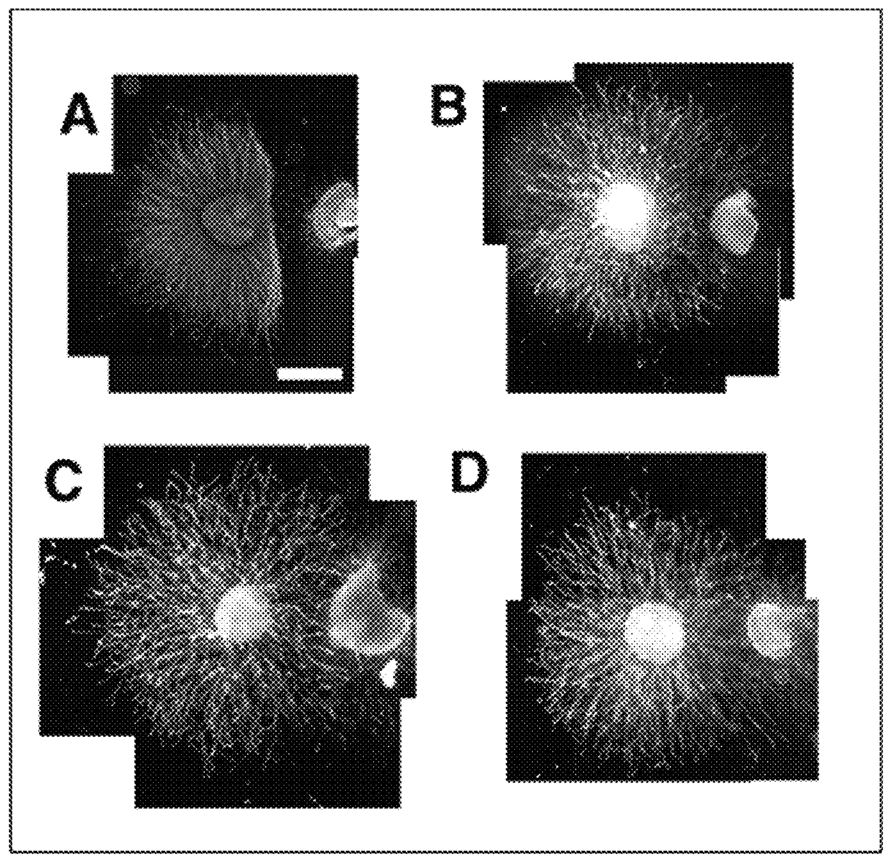
FIG. 4 shows microscope images for illustrating the result of a DRG-spinal explant coculture assay. A is a microscope image for illustrating the result of the coculture assay on a dorsomedial spinal explant and DRG in an NGF-supplemented medium. B is a microscope image for illustrating the result of the coculture assay on a dorsal spinal explant and DRG in an NGF-supplemented medium. C is a microscope image for illustrating the result of the coculture assay on a dorsomedial spinal explant and DRG in an NT-3-supplemented medium. D is a microscope image for illustrating the result of the coculture assay on a dorsal spinal explant and DRG in an NT-3-supplemented medium.
Figure 5:
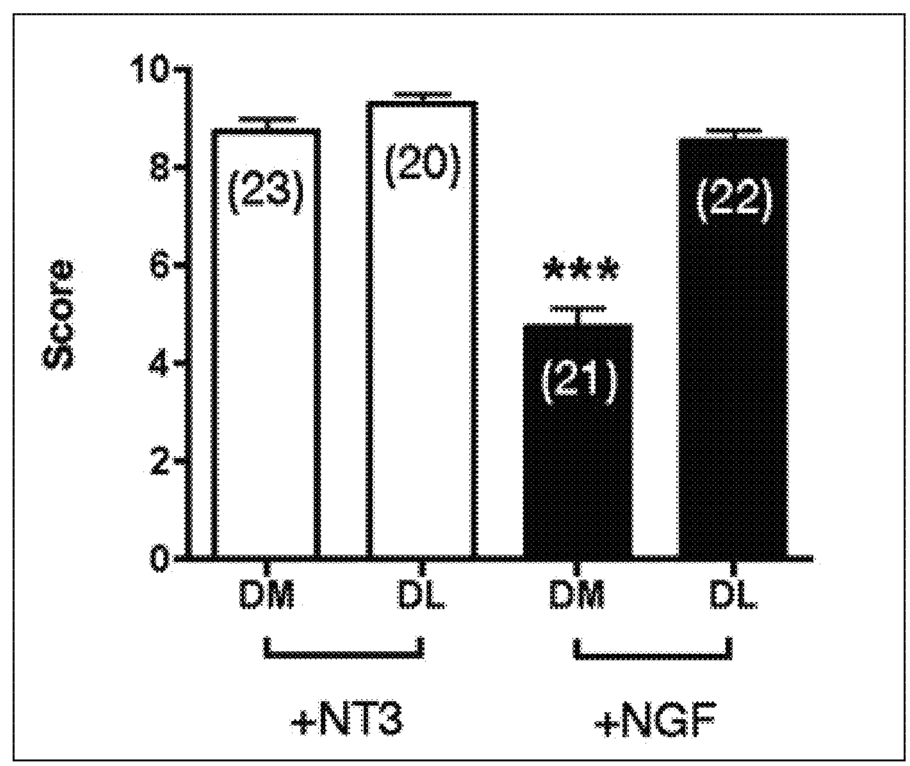
FIG. 5 is a graph for illustrating the result of the DRG-spinal explant coculture assay.

In order to verify that PtdGlc or a derivative thereof is a signaling molecule for DRG sensory nerves and acts as a chemorepellent particularly on a TrkA-expressing neuron as described above, organotypic spinal cord/DRG explant culture assay was conducted. A dorsal root ganglion (DRG) explant having a diameter of approximately 250 μm was cultured on a 3-D collagen matrix together with an explant obtained by dissecting the spinal cord. Then, 48 hours after the co-culturing, DRG axon extension was observed. Note that in the present Example, the explant from the spinal cord was dissected and separated into ones derived from dorsal (Dorsolateral, DL) or dorsomedial (DM) side, in other words, sites where the PtdGlc content is low (DL) or high (DM), for use (see FIGS. 2 and 3). FIGS. 4 and 5 show the obtained result. Note that the white line in FIG. 4 is a scale bar representing a length of 500 μm, the numerical values in parentheses in FIG. 5 indicate the number of DRG explants assayed, and a column with three asterisks indicates $P<0.001$ (Kruskal-Wallis test with Dunnett's post-test).

As apparent from the result shown in FIGS. 4 and 5, in a medium supplemented with NGF, the DRG axon radially extended, but the extension was repelled (regressed) by the explant from the dorsomedial spinal cord. However, such an influence was not observed from the explant from the dorsal spinal cord (see B and D in FIG. 4, and FIG. 5). The repellent effect of the explant from the dorsomedial spinal cord was not observed on the cultured DRG axon supplemented with NT-3 (see C in FIG. 4, and FIG. 5).

Thus, it was revealed that PtdGlc or a diffusible derivatives thereof demonstrated a chemorepellent effect specifically on an NGF-dependent axon extension, in other words, a neuron expressing TrkA or the like, an NGF receptor. Meanwhile, it was also revealed that PtdGlc or the like did not influence NT-3-dependent axon extension, in other words, a neuron expressing TrkC or the like, an NT-3 receptor.

Example 3

Figure 6:
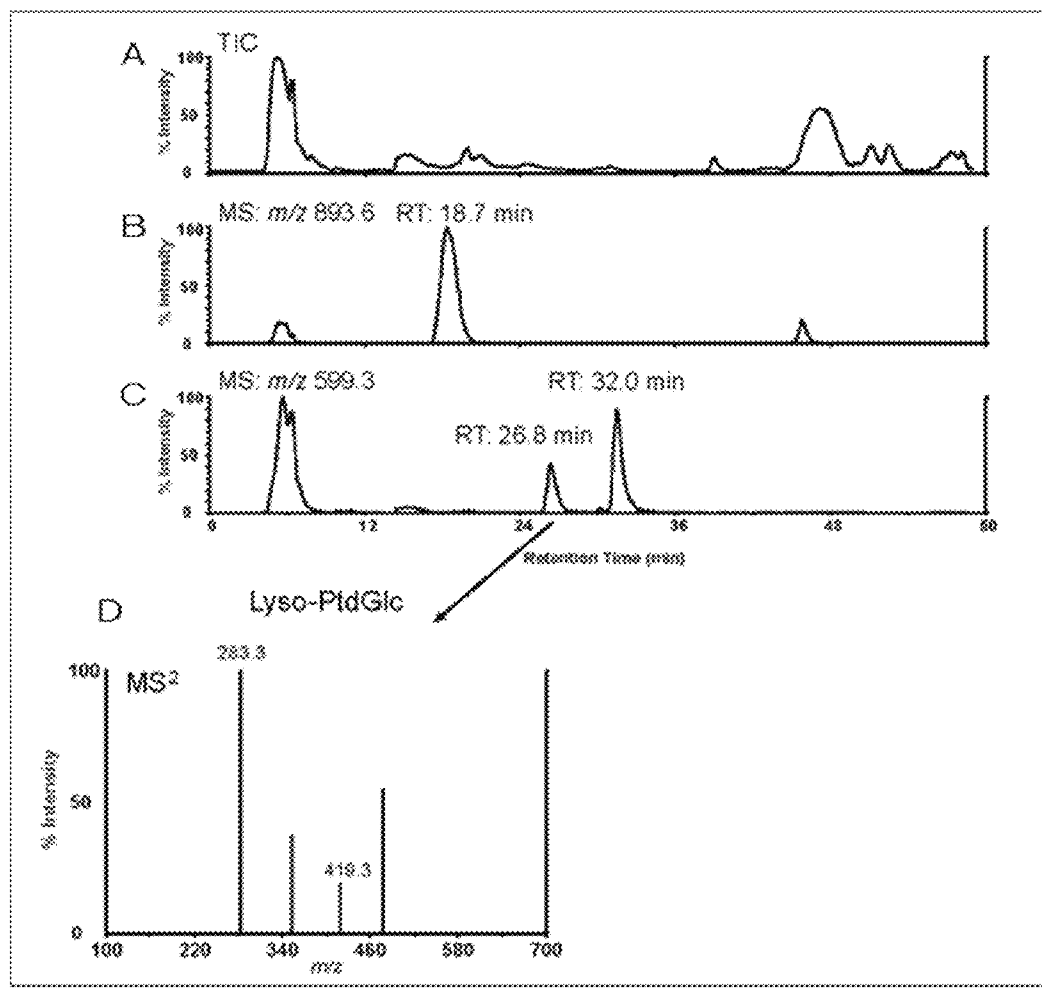
FIG. 6 shows graphs for illustrating the result of analyzing glial cells derived from a chicken embryo at HH St. 35 and the culture supernatant with LC/MS/MS. A shows a total ion mass chromatogram, B shows a mass chromatogram with a molecular weight of 893.6, and C shows a mass chromatogram with a molecular weight of 599.3. Moreover, a peak in the middle of the mass chromatogram in B represents PtdGlc, and peaks in the middle of the mass chromatogram in C represent Lyso-PtdGlc on the left (retention time (RT): 26.8 minutes) and Lyso-PtdIns (Lysophosphatidylinositol) on the right (RT: 32.0 minutes). D shows the fragmentation profile obtained by analyzing the peak of Lyso-PtdGlc by MS/MS. Note that peaks at m/z values of 283.3 and 419.3 in D correspond to structures shown in FIG. 7.
Figure 8:
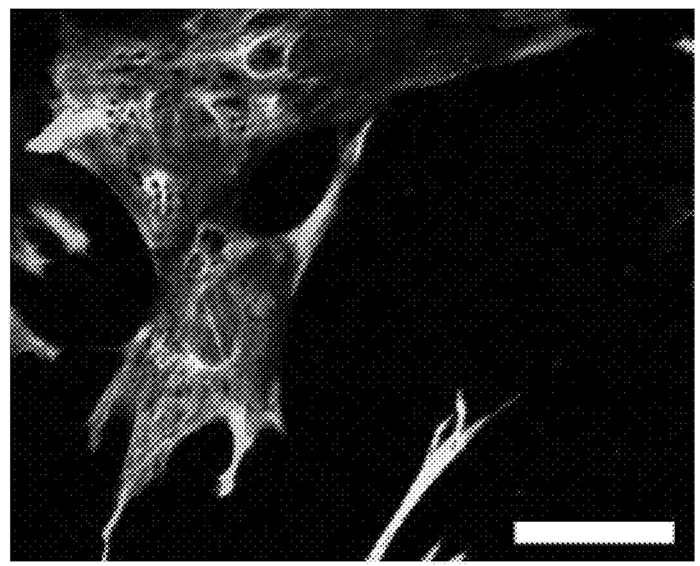
FIG. 8 shows a microscope image for illustrating the result of analyzing glial cells derived from a chicken embryo at HH St. 35 by an immunostaining method using an anti-transitin antibody, an anti-PtdGlc antibody, and Hoechst 33258.
Figure 9:
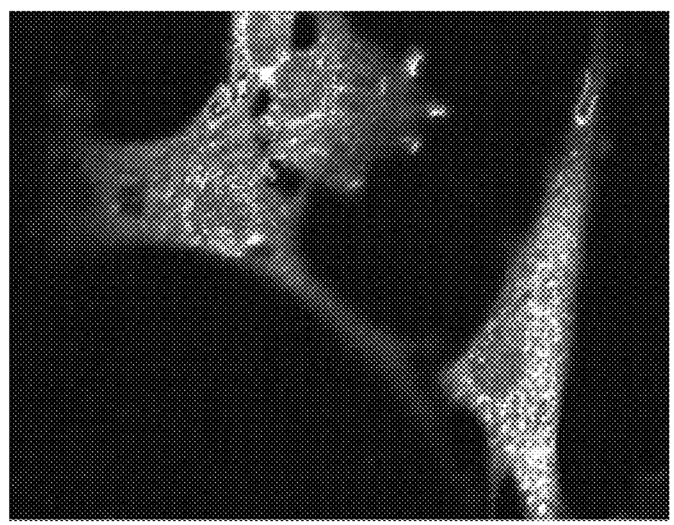
FIG. 9 shows a microscope image for illustrating the result of analyzing the glial cells derived from the chicken embryo at HH St. 35 by the immunostaining method using an anti-GFAP antibody, an anti-PtdGlc antibody, and Hoechst 33258.

As described in Example 1, PtdGlc is widely expressed in the white matter (see FIG. 2). Thus, it is predicted that the PtdGlc supply source in the spinal cord is not neurons. For this reason, in order to confirm that such a prediction is reasonable, glia in the spinal cord were analyzed by mass spectrometry. Specifically, proliferative glial cells were isolated from the spinal cord at HH St. 35, and cultured for 7 days in vitro. After the culturing was finished, the glial cells and the culture supernatant were analyzed with a nano-liquid chromatography-tandem mass spectrometer (nano-LC/MS/MS). FIG. 6 shows the obtained result. Moreover, using such a glial cell culture, immunostaining was performed instead of the mass spectrometry. FIGS. 8 and 9 show the obtained result. Note that in FIG. 8, a portion emitting green fluorescence indicates a region labelled with an anti-trans it in antibody, and the white line is a scale bar, representing a length of 10 μm. Moreover, in FIG. 9, a portion emitting green fluorescence indicates a region labelled with an anti-GFAP antibody. Further, in FIGS. 8 and 9, a portion emitting blue fluorescence indicates a region stained with Hoechst 33258, that is, a cell nucleus, and a portion emitting red fluorescence indicates a region labelled with an anti-PtdGlc antibody.

Figure 7:
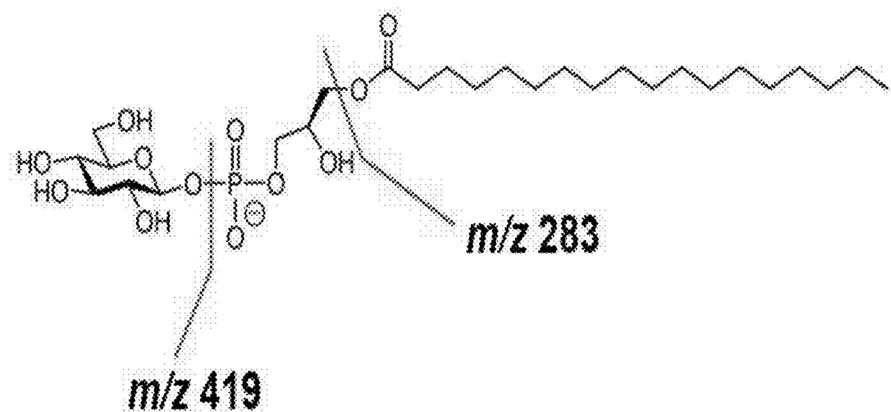
FIG. 7 is a conceptual drawing showing the chemical structural formula of Lyso-PtdGlc and m/z values of putative fragment ions.

As apparent from the result shown in FIG. 6 of analyzing the glial cells and the culture supernatant using the nano-liquid chromatography-tandem mass spectrometer (nano-LC/MS/MS), peaks (m/z 283.3, m/z 419.3) of putative fragment ions characteristic of Lyso-PtdGlc shown in FIG. 7 were observed. This result revealed that the glial cells produced PtdGlc, and that the culture supernatant of the glial cells contained lysophosphatidylglucoside (Lyso-PtdGlc), that is, PtdGlc with the acrylic chain at the sn-2 position hydrolyzed.

Moreover, as apparent from the result shown in FIGS. 8 and 9, half of the glial cell culture was double-stained with a DIM21 antibody and an anti-GFAP antibody, and observed to be cultured cells expressing PtdGlc and GFAP, a marker of star-shaped astrocyte. In addition, the remaining half of the cultured cells was double-stained with a DIM21 antibody and an EAP3 antibody, and observed to be glial cells expressing transitin and PtdGlc (Note that the EAP3 antibody is a transitin-specific antibody, and transitin is a homolog of avian nestin known as a marker of radial glial cells and neural progenitor cells of mammals).

Thus, from the results of such a biochemical analysis and double immunostaining, it is apparent that radial glial cells or glia-like cells in the spinal cord contain PtdGlc. Moreover, it was suggested that the glial cells produced or released a water-soluble derivative Lyso-PtdGlc to the extracellular environment.

Example 4

Next, an antibody against Lyso-PtdGlc specific was produced. Specifically, an anti-Lyso-PtdGlc-specific monoclonal antibody (antiserum) was produced using Lyso-PtdGlc as an antigen obtained by isolation or synthesis based on a method described later, and employing the ADLib (Autonomously Diversifying Library) system developed by Chiome Bioscience Inc. (RIKEN, Japan, Genetic Dynamic Research Unit) (see Seo H. et al. Nat. Biotechnol. 23, 731-735 (2005) and Seo H. et al. Nat. Protocols. 1, 1502-1506 (2006)).

<Synthesis of Lyso-PtdGlc>

Lyso-PtdGlc used as an antigen was obtained by hydrolyzing PtdGlc obtained by isolation or synthesis using phospholipase A2 (PLA2). Specifically, first, PtdGlc was obtained by isolation from as described in NPL 32, the brain of a rat fetus, or by chemical synthesis as described in Greimel, M. et al. Bioorg Med Chem 16, 7210-7 (Aug. 1, 2008).

Next, 50 to 100 nmol of PtdGlc obtained by isolation or synthesis (the phosphorus content was estimated using ascorbate reduction assay described in P. S. Chen, T. Y. Toribara, H. Warner, Anal Chem 28, 1756-1758 (November 1956)) was digested with 10 μg of bee venom-derived PLA2 (manufactured by Sigma-Aldrich Corporation) in 20 μl of TritonX-100-containing Tris-HCl buffer (0.1% TritonX-100-containing Tris-HCl (pH 7.6, 50 mM)) at 37° C. for 1 hour. Note that the structure of the digestion product was observed by TLC. When the hydrolysis was insufficient, a new enzyme was added to the digestion product, and the digestion reaction was repeated. After the digestion reaction, the reaction product was dried under nitrogen gas flow, re-dissolved in a chloroform/methanol mixture solution (4:1 (v/v)), and added into an iatrobead-filled column (bed volume: approximately 1 ml) having being equilibrated in advance with the above mixture solution. After washing with a chloroform/methanol mixture solution, 5 times volume of a chloroform/methanol mixture solution (2:1, 1:1, 1:2) and pure methanol was added stepwise thereto to elute a matter adsorbed to the column. The eluted fractions were dried under nitrogen gas flow and checked by TLC. Most of PtdGlc was eluted into a chloroform/methanol (2:1) fraction, and LysoPtdGlc was recovered from the chloroform/methanol (1:1 and 2:1) fraction. When the fractionation was insufficient, the Lyso-PtdGlc-containing fraction was retreated with the same column. LysoPtdGlc thus recovered was estimated based on the phosphorus content, and dispensed into a 12×32-mm glass screw vial (manufactured by Waters Corporation) in such a manner that approximately 1 nmol aliquot was contained. The LysoPtdGlc was stored at −80° C. until use (note that the stored LysoPtdGlc was used with 3 weeks from the preparation).

Example 5

Figure 10:
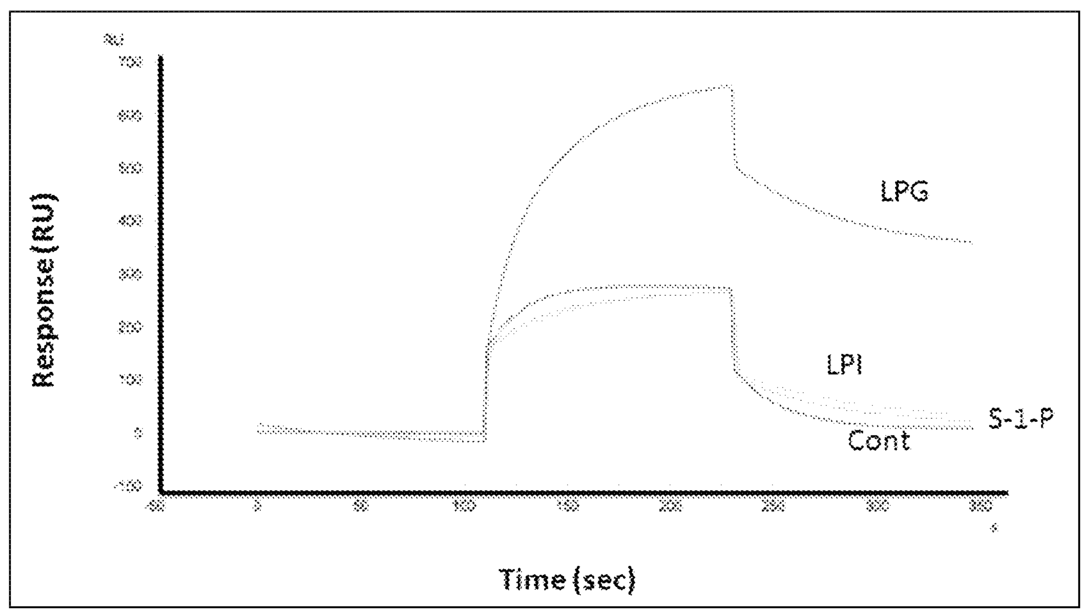
FIG. 10 is a graph for illustrating the result of analyzing the binding activity of an anti-Lyso-PtdGlc antibody by surface plasmon resonance measurement.

Next, the binding activity (binding strength, speed, selectivity) of the Lyso-PtdGlc-specific antibody obtained in Example 4 was analyzed by surface plasmon resonance measurement. Specifically, according to a predetermined protocol of Biacore (manufactured by GE Healthcare), first, a sensor chip (HPA) was washed with octyl glucoside, and then coated with the antigen liposome. Note that as the antigen fixed to the sensor chip in this manner, LPG, LPI (lysophosphatidylinositol) and S-1-P (sphingosine-1-phosphate) were used. Next, a solution of the Lyso-PtdGlc-specific antibody obtained in Example 4 (100 μg/ml) was sent to the sensor chip with the antigen fixed, and then a Biacore running buffer (HBS-N) was passed therethrough. Subsequently, from the change in response in this process (the shape of a sensorgram: formation of the antigen and the antibody, and dissociation of the antigen and the antibody), the association rate constant ($k_a$) and the dissociation rate constant ($k_d$) were calculated by curve fitting. Furthermore, from these constants the affinity (dissociation constant: $K_D$) was obtained. FIG. 10 shows the obtained result (sensorgram).

As a result of analyzing the Lyso-PtdGlc-specific antibody obtained in Example 4 by the surface plasmon resonance measurement, the antibody most strongly reacted with LPG ($K_D$: $10^{-8}$ M order), and the binding activity to the other lyso form (LPI) having a structure similar to that of LPG was approximately 1/10 thereof.

Example 6

Figure 11:
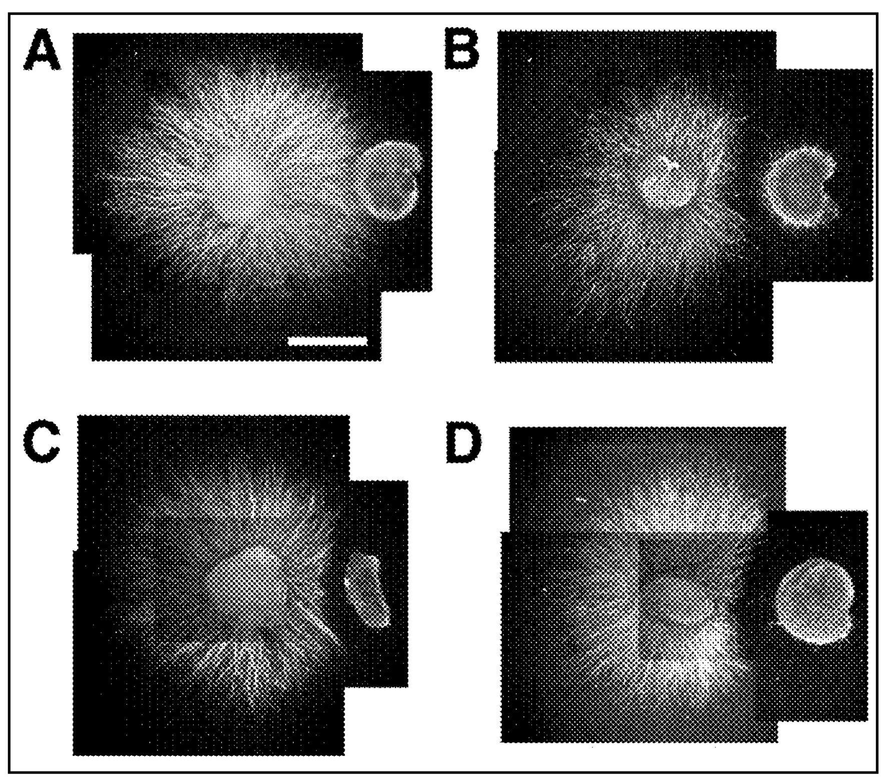
FIG. 11 shows microscope images for illustrating the result of a dorsomedial spinal explant-DRG coculture assay in the presence of antibodies. A is a microscope image for illustrating the result of the coculture assay in the presence of an anti-Lyso-PtdGlc antibody and an anti-NRP-1 antibody. B is a microscope image for illustrating the result of the coculture assay in the presence of an anti-Lyso-PtdGlc antibody. C is a microscope image for illustrating the result of the coculture assay in the presence of an anti-NRP-1 antibody. D is a microscope image for illustrating the result of the coculture assay in the presence of a control antibody (IgM).
Figure 12:
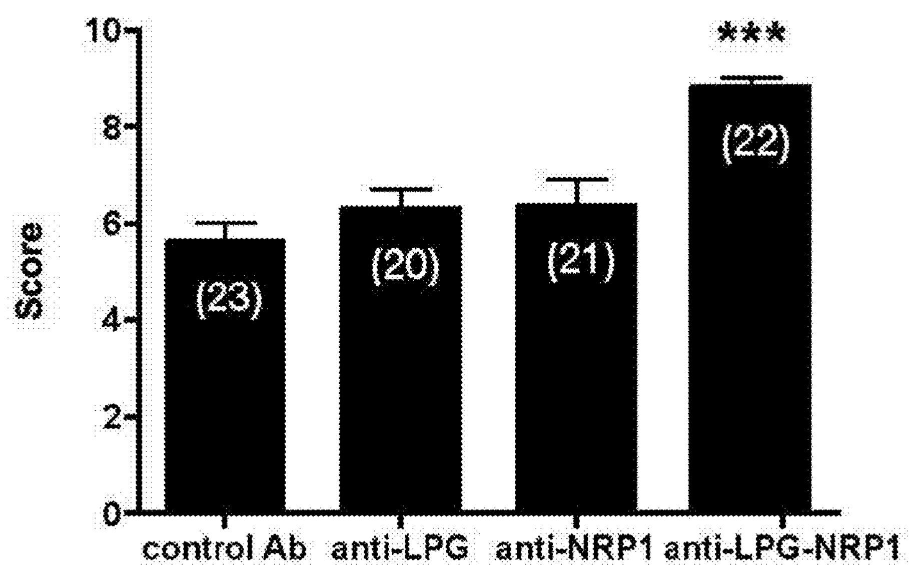
FIG. 12 is a graph for illustrating the result of the dorsomedial spinal explant-DRG coculture assay in the presence of antibodies.

Next, the function inhibitory activity of the Lyso-PtdGlc-specific antibody obtained in Example 4 was examined using a collagen gel coculture assay. However, initially, even when the anti-Lyso-PtdGlc antibody was added to the culture system, only a slight suppressing effect on the chemorepellent effect demonstrated by the dorsomedial spinal cord explant (statistically non-significant reduction in the chemorepellent activity) was observed. Hence, since Sema3A is also expressed in the dorsal spinal cord during the chicken early development (see NPL 15), a few Sema3A-expressing cells or the Sema3A protein itself that hardly disappears remain in the explant from the dorsal spinal cord, which may have influenced the above assay system. For this reason, an antibody capable of functionally inhibiting neuropilin-1 (NRP-1 antibody, added at a concentration: 4 μg/ml, AF566, manufactured by R&D SYSTEMS, INC.) was added into the medium to perform the assay again. Note that neuropilin-1 is a receptor of Sema3A ligand in the Sema3A signal transduction. FIGS. 11 and 12 show the obtained result. Note that the white line in FIG. 11 is a scale bar representing a length of 500 μm, the numerical values in parentheses in FIG. 12 indicate the number of growth cones assayed, and a column with three asterisks indicates $P<0.001$ (Kruskal-Wallis test with Dunnett's post-test).

As apparent from the result shown in FIGS. 11 and 12, in the situation where the function of NRP-1 receptor was inhibited, the anti-Lyso-PtdGlc (LPG) antibody (5 μg/ml) reduced the chemorepulsive activity of the dorsomedial spinal cord explant on DRG axon extension by 1/3 or more (see A in FIG. 11 and FIG. 12). Note that a statistically significant influence on the chemorepulsive activity was not observed by the addition of the anti-Lyso-PtdGlc (LPG) antibody or the anti-NRP-1 antibody alone (see B and C in FIG. 11). Moreover, even when a control Ab (IgM, manufactured by Diaclone Immunology) was added at the same concentration, no influence on the chemorepulsive action demonstrated by the explant from the dorsomedial spinal cord was observed (see D in FIG. 11).

Example 7

Figure 13:
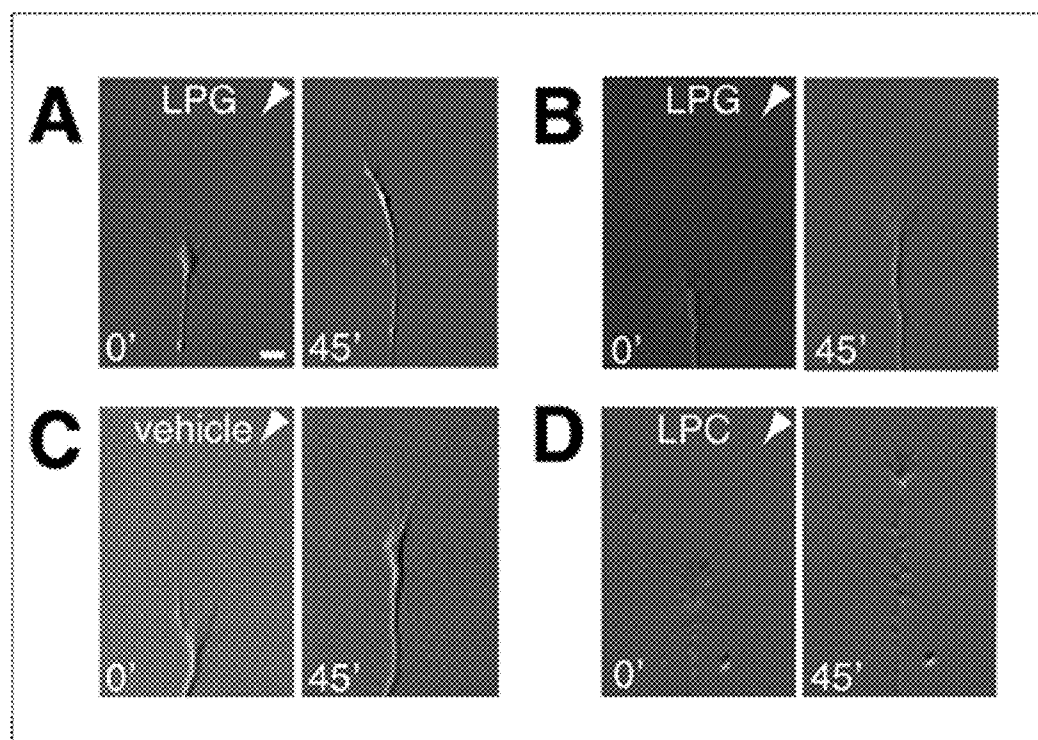
FIG. 13 shows microscope images for illustrating the result of a growth cone turning assay. A is a microscope image for illustrating the result of the growth cone turning assay on a DRG-derived neuron (TrkCn) in an NGF-supplemented medium in the presence of an LPG concentration gradient. B is a microscope image for illustrating the result of the growth cone turning assay on a DRG-derived neuron (TrkCn) in an NT-3-supplemented medium in the presence of an LPG concentration gradient. C is a microscope image for illustrating the result of the growth cone turning assay on an NGF-treated DRG-derived neuron with in the presence of a vehicle (1% v/v methanol/PBS). D is a microscope image for illustrating the result of the growth cone turning assay on an NGF-treated DRG-derived neuron in the presence of an LPC concentration gradient.
Figure 14:
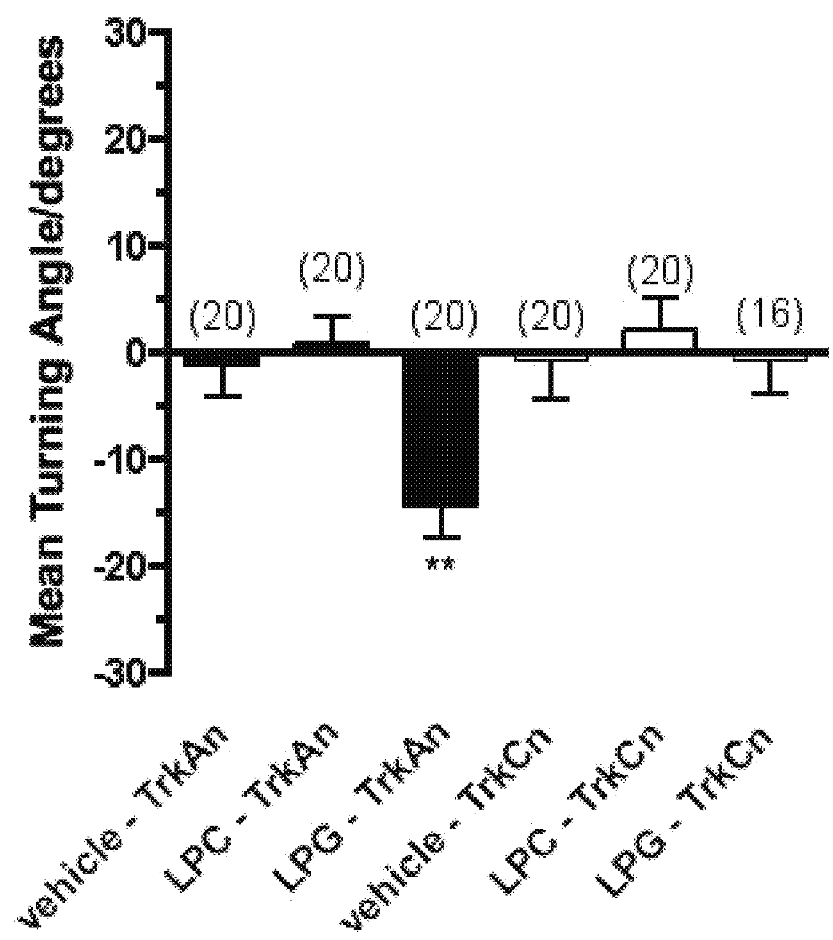
FIG. 14 is a graph for illustrating the result of the growth cone turning assay.
Figure 15:
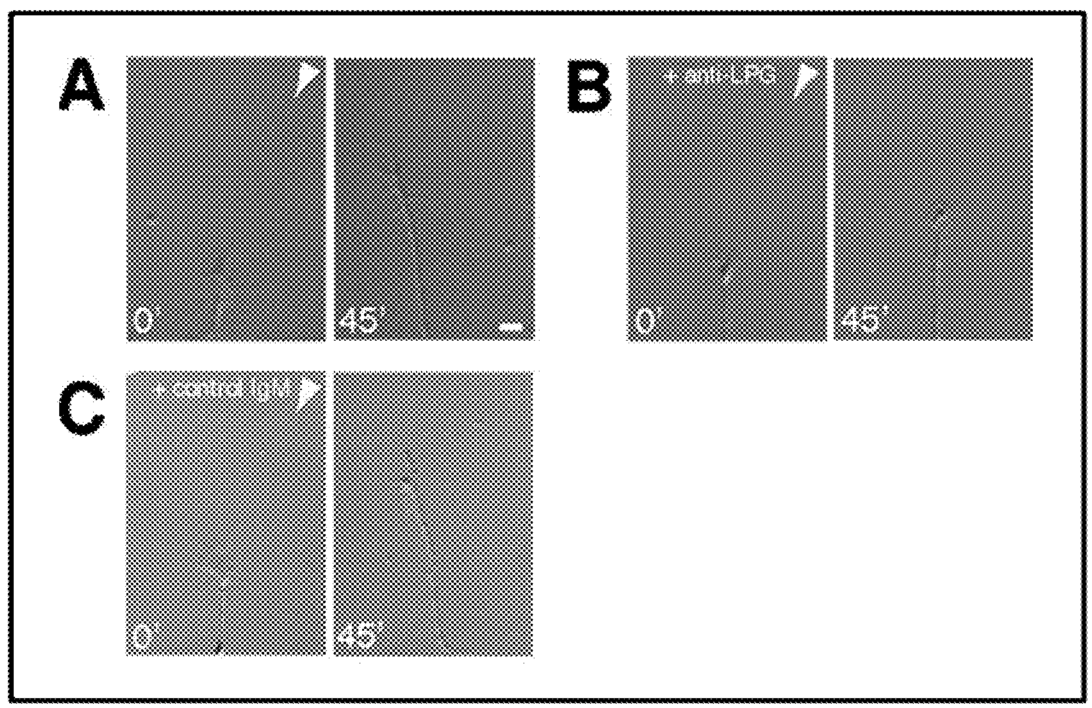
FIG. 15 shows microscope images for illustrating the result of a growth cone turning assay in the presence of antibodies. A is a microscope image for illustrating the result of the DRG-derived neuron growth cone turning assay in the presence of an LPG concentration gradient. B is a microscope image for illustrating the result of the growth cone turning assay on a DRG-derived neuron in the presence of an anti-Lyso-PtdGlc antibody and an LPG concentration gradient. C is a microscope image for illustrating the result of the growth cone turning assay on a DRG-derived neuron in the presence of a control antibody (IgM) and an LPG concentration gradient.
Figure 16:
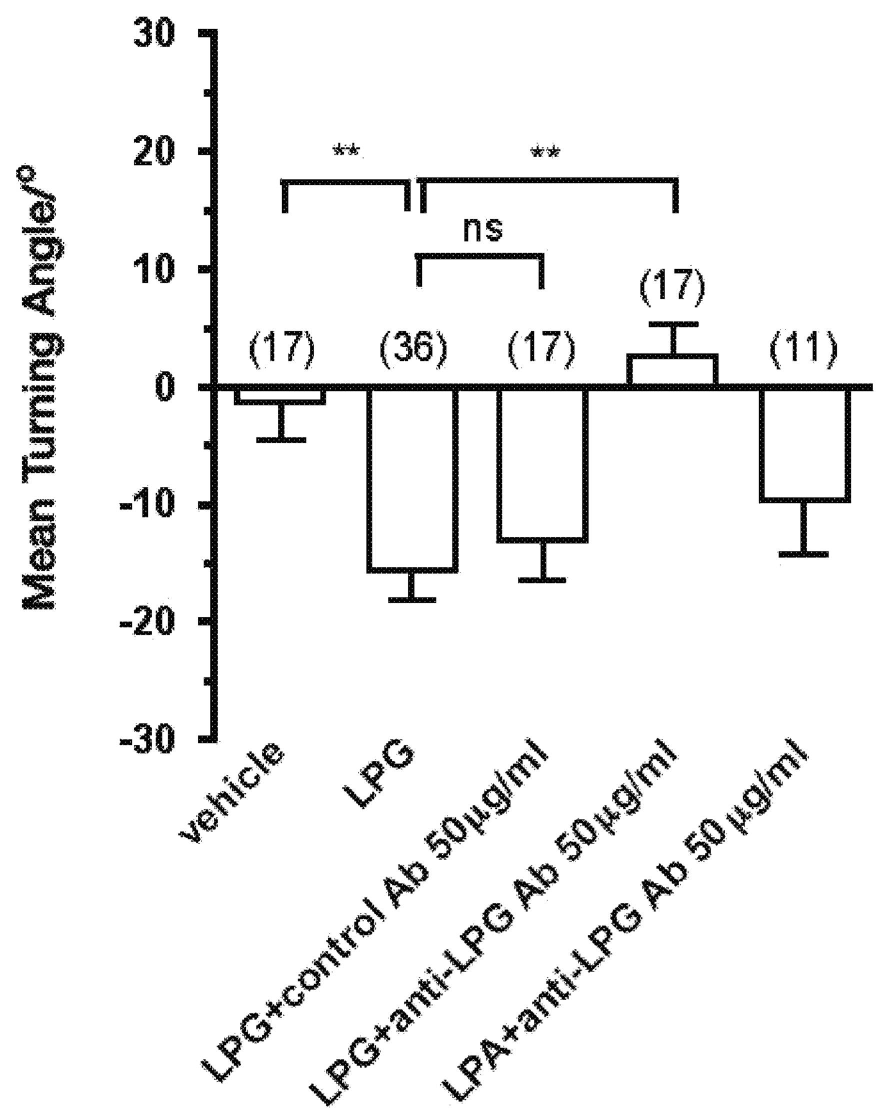
FIG. 16 is a graph for illustrating the result of the growth cone turning assay in the presence of the antibody.

Next, the chemorepulsive action of Lyso-PtdGlc on the growth cone of an NGF-dependent neuron or an NT-3-dependent neurons was examined using an in vitro turning assay. FIGS. 13 and 14 show the obtained result. Moreover, the chemorepulsive action of Lyso-PtdGlc on the growth cone of an NGF-dependent neuron in the presence of the anti-Lyso-PtdGlc antibody was examined using the in vitro turning assay. FIGS. 15 and 16 show the obtained result. Note that the white lines in FIGS. 13 and 15 are scale bars representing a length of 5 μm, the numbers in FIGS. 13 and 15 indicate the time (unit: minute) from the increase in the concentration gradient of LPG or the like, and the arrow head (triangle) in FIGS. 13 and 15 indicates a site where the concentration gradient of LPG or the like was increased. Moreover, the numerical values in parentheses in FIGS. 14 and 16 indicate the number of growth cones assayed, and a column with two asterisks indicates $P=0.0063$ (1-Way ANOVA with Dunnett's multiple comparison post-test).

As apparent from the results shown in FIGS. 13 and 14, it was revealed that the axon extended from a HH St. 28 chicken DRG-derived neuron (axon extended from TrkAn (TrkA neuron)) in an NGF-supplemented medium changed its extension direction specifically to the microscopic concentration gradient of Lyso-PtdGlc having a chemorepulsive action (see A in FIG. 13). Meanwhile, in an NT-3-supplemented medium in place of NGF, no significant change in the extension direction (angle) of the axon extended from the neuron (axon extended from TrkCn (TrkC neuron)) was observed (see B in FIG. 13). Moreover, by the addition of a vehicle (1% v/v methanol-containing PBS) alone or the concentration gradient of LPC (lysophosphatidylcholine) alone, no significant influence on the axon extension of the neuron (TrkAn or TrkCn) treated with NGF or NT-3 was observed (see C and D in FIG. 13. Note that NT-3-treated neurons were unillustrated). Further, as apparent from the result shown in FIGS. 15 and 16, when the anti-Lyso-PtdGlc antibody was added into an NGF-supplemented medium in such a manner that the concentration in a culture tank was 50 μg/ml 30 minutes before the Lyso-PtdGlc concentration gradient was caused, the suppression of the change in the extension direction of the DRG-derived neuron was observed (see B in FIG. 15). Meanwhile, even when the control IgM antibody was added at the same concentration as above, no influence on the change in the extension direction of the DRG-derived neuron was observed (see C in FIG. 15).

Nevertheless, such a result may have been obtained due to a physical influence of the antibody treatment on the organelle of the growth cone necessary to demonstrate the chemorepulsive action against turning. Hence, the influence of the anti-Lyso-PtdGlc antibody on the chemorepulsive action demonstrated by LPA (lysophosphatidic acid) was examined. Note that LPA has been revealed to demonstrate a chemorepellent effect in a growth cone turning (see X. B. Yuan et al., Nat Cell Biol 5, 38-45 (January, 2003)). As apparent from the result shown in FIG. 16, even though 50 μg/ml of the anti-Lyso-PtdGlc antibody was added to the culture system, the extension direction (angle) of the growth cone was changed by the LPA concentration gradient. A strong chemorepellent effect of LPA was observed.

Thus, it was revealed that in the in vitro experimental system using a single neuron, exogenous Lyso-PtdGlc demonstrated a chemorepellent effect specifically on a TrkA axon.

Example 8

Figure 17:
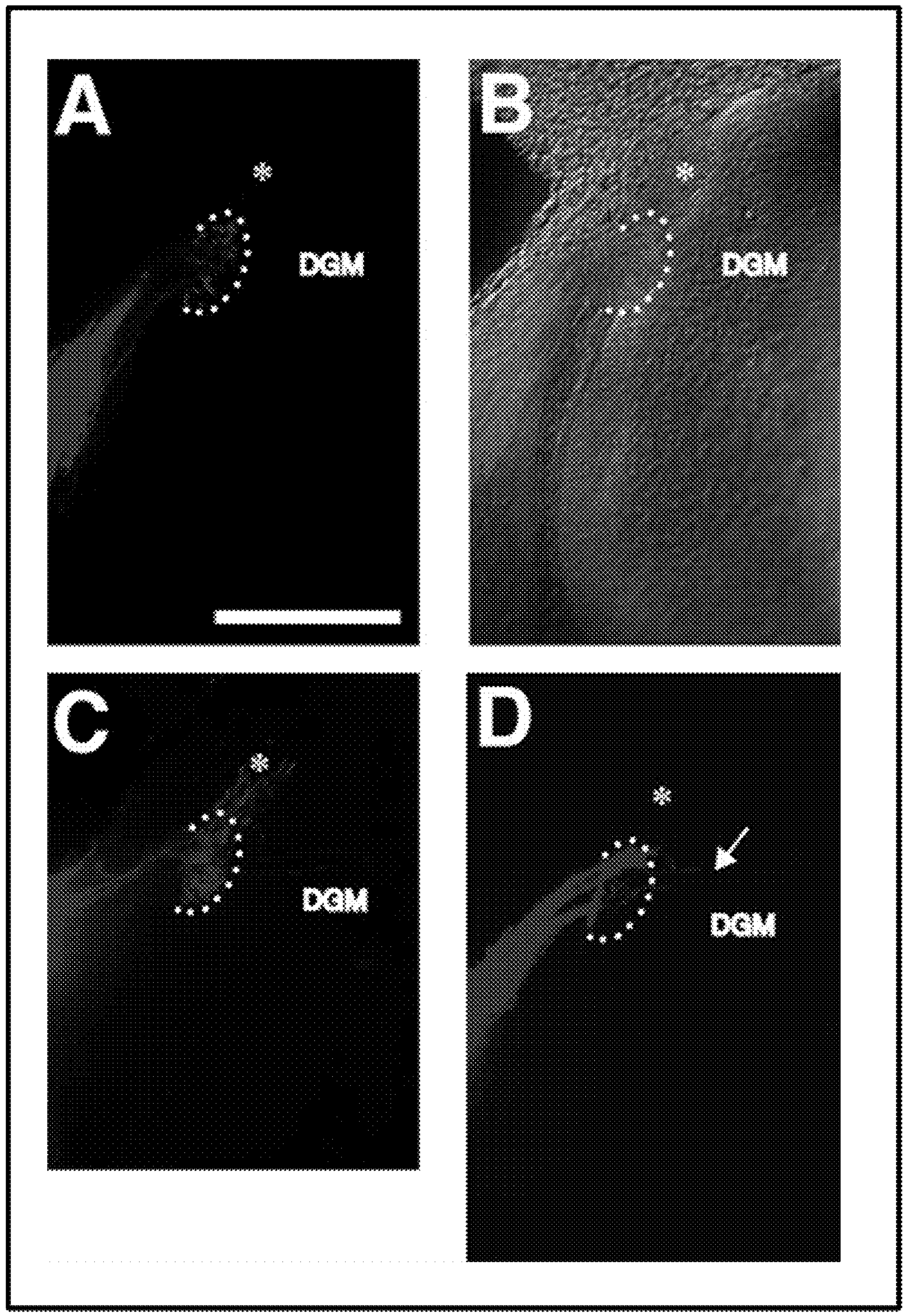
FIG. 17 shows microscope images of chicken embryos (HH St. 28) into which antibodies were injected. A is a microscope image of a chicken embryonic spinal cord into which a control antibody and DiI were injected. B is an observation image obtained by superimposing a DIC image on the microscope image shown in A. C is a microscope image for illustrating an ectopic deployment of a TrKA axon into the dorsal white matter of a chicken embryonic spinal cord into which an anti-Lyso-PtdGlc antibody and DiI were injected. D is a microscope image for illustrating an abnormal projection of a DRG axon into the spinal cord gray matter of a chicken embryonic spinal cord into which the anti-Lyso-PtdGlc antibody and DiI were injected.

Next, the chemorepellent effect specific to a TrkA neuron demonstrated by Lyso-PtdGlc observed in an in vitro system was observed in an in vivo system. Specifically, in order to inhibit Lyso-PtdGlc signal transduction in an experimental animal, the antibody having a function inhibitory activity, an anti-Lyso-PtdGlc antibody, was injected into the embryonic spinal cord. Note that as described in Examples 6 and 7, it is apparent from the collagen gel coculture and in vitro growth cone turning assays that the anti-Lyso-PtdGlc antibody is an antibody having a function inhibitory activity. FIG. 17 and Table 1 show the obtained result. Note that a site surrounded by the dotted line in FIG. 17 indicates the oval bundle of His, and the asterisk indicates a site where a TrkC-expressing neuron preferentially exists. Moreover, "DGM" in FIG. 17 indicates a dorsal grey matter.

TABLE 1

| Antibody | Abnormal axon projection | Normal |
|---|---|---|
| Anti-LysoPtgGlc antibody | 16 | 4 |
| Control IgM | 1 | 11 |

As apparent from the result shown in FIG. 17 and Table 1, Lyso-PtdGlc function inhibition in vivo at HH Sts. 23 to 26 disturbed the pattern formation of growth cone of a sensory afferent nerve during the development stage of the spinal cord, and mainly two abnormalities were observed in the axon projection. The first is abnormal projection of a DRG axon into the spinal cord gray matter (see D in FIG. 17), and the second is ectopic deployment of a TrkA axon into a region of the dorsal white matter where normally a TrkC neuron preferentially exists (see C in FIG. 17). The abnormal pattern formation of a sensory afferent nerve in the spinal cord was observed in 16 out of 20 embryos into which the antibody, having a function inhibitory activity was injected (80%). The axon deployment into the dorsal white matter was clearly observed in 2 embryos (10%). The abnormal projection of an axon into the dorsal horn gray matter was observed in 9 embryos (45%). Both of the main two abnormalities were observed in 5 embryos (25%). Meanwhile, among 12 embryos into which a control antibody was injected, normal axon extension and the like were observed in 11 embryos (92%), while abnormal axon projection was observed in only one embryo.

Thus, it was revealed that in the dorsal spinal cord during the early development process, Lyso-PtdGlc-related signal transduction was essential for the accurate axon projection and the pattern formation of a sensory afferent nerve in vivo also. Moreover, as apparent from the descriptions in Examples 5 to 8, the anti-Lyso-PtdGlc antibody of the present invention is a very excellent antibody in that the antibody shows a quite excellent specificity to lysophosphatidylglucoside and inhibits a repellent (regressive) action of lysophosphatidylglucoside on neuron axon extension.

Note that hybridomas (ADLib#7 and ADLib#15) producing the anti-Lyso-PtdGlc antibody have been deposited at NITE Patent Microorganisms Depositary (NPMD), Incorporated Administrative Agency Nat lanai Institute of Technology and Evaluation (NITE) (2-5-8, Kazusakamatari, Kisarazu-shi, Chiba, postal code 292-0818, Japan) since Apr. 21, 2010. Clone numbers of deposited clones thereof and deposit numbers assigned are NITE P-939 and NITE P-940.

Example 9

Figure 18:
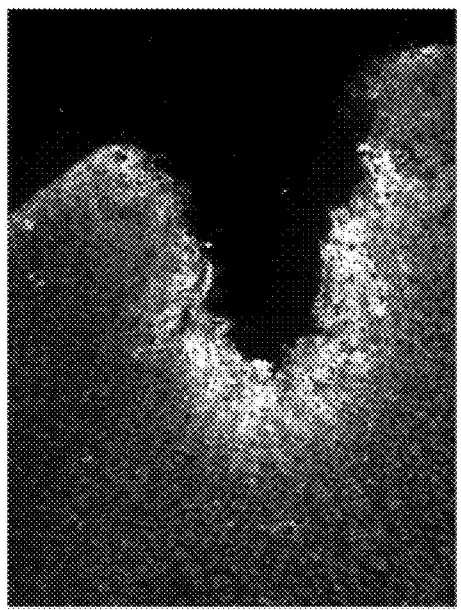
FIG. 18 shows a microscope image for illustrating the result of analyzing the brain of an adult mouse having a damaged central nerve by an immunostaining method using an anti-Lyso-PtdGlc antibody.
Figure 19:
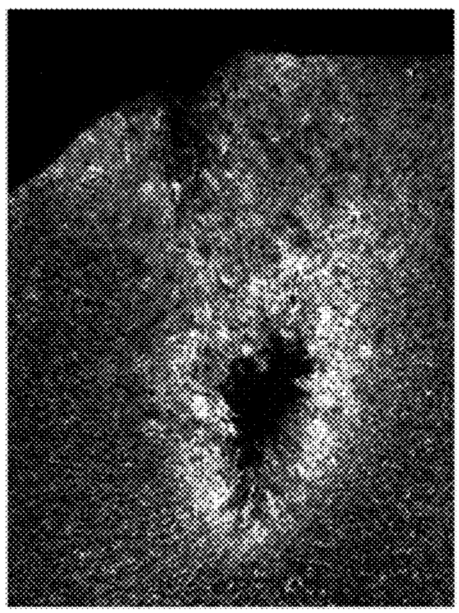
FIG. 19 shows a microscope image for illustrating the result of analyzing the brain of an adult mouse having a damaged central nerve by the immunostaining method using the anti-Lyso-PtdGlc antibody, the mouse being different from the mouse shown in FIG. 18.
Figure 20:
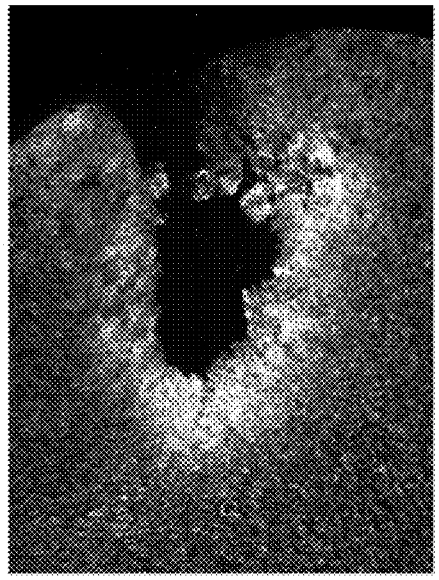
FIG. 20 shows a microscope image for illustrating the result of analyzing the brain of an adult mouse having a damaged central nerve by the immunostaining method using the anti-Lyso-PtdGlc antibody, the mouse being different from the mice shown in FIGS. 18 and 19.
Figure 21:
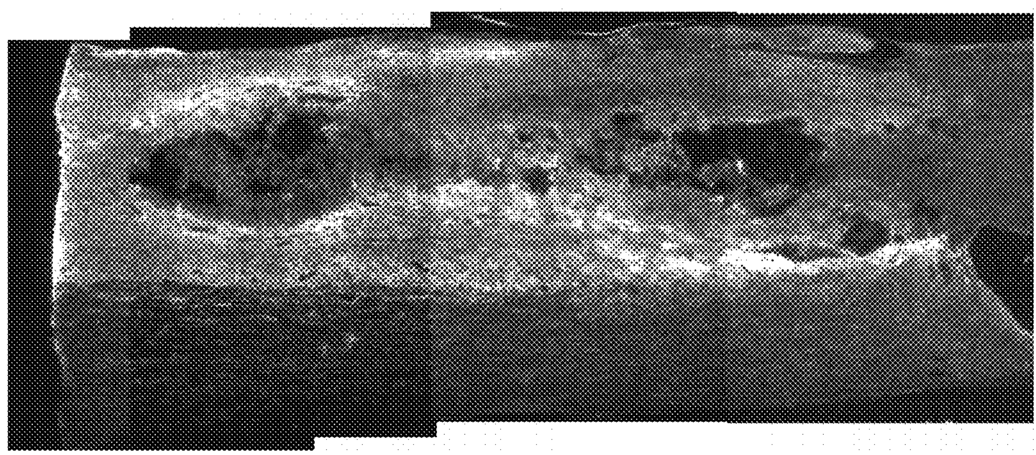
FIG. 21 shows microscope images for illustrating the result of analyzing the spinal cord of an adult rat having a damaged central nerve by the immunostaining method using the anti-Lyso-PtdGlc antibody.

Next, examined was PtdGlc expression in a damaged central nervous system of an adult animal. Specifically, the brains of adult mice (one month after birth) were stabbed with a tip of a cotton swab for children and damaged. One week later, immunostaining was conducted using a DIM21 antibody to examine the degree of PtdGlc expression at the damaged sites. FIGS. 18 to 20 show the obtained result. Moreover, the spinal cords of adult rats (weight: approximately 250 grams) were epidurally damaged by a standard method for Multi Centre Animal Spinal Cord Injury Study (J. A. Gruner, J. Neurotrauma 9, 123-128, 1992). Two weeks later, immunostaining was conducted using a DIM21 antibody to examine the degree of PtdGlc expression at the damaged sites. Note that it has been observed that the amount of PtdGlc expressed is quite small in the central nervous system of normal adult mouse and adult rat (see NPL 32). FIG. 21 shows the obtained result.

As apparent from the results shown in FIGS. 18 to 21, the expression was enhanced specifically at the damaged sites in the central nervous systems of the adults. Such enhancement is likely to lead to a possibility that Lyso-PtdGlc, a hydrolysate of PtdGlc, inhibits repairing (axon extension) of a neural circuit at the damaged site as described above. Therefore, it is apparent that addition of the antibody of the present invention (anti-Lyso-PtdGlc antibody) to the damaged site in the adult central nerve is highly likely to promote of repairing of a neural circuit at the site.

INDUSTRIAL APPLICABILITY

The present invention provides: an antibody capable of suppressing a repellent effect of lysophosphatidylglucoside on axon extension of a neuron; and a composition for suppressing a repellent effect of lysophosphatidylglucoside on axon extension of a neuron, the composition comprising the antibody as an active ingredient. The antibody and the composition of the present invention are capable of promoting repairing of a neural circuit in nervous system disorders, neurodegenerative disorders, and neuronal damages. Accordingly, the present invention can contribute greatly to the medical field and so on.

REFERENCE TO DEPOSITED BIOLOGICAL MATERIAL

1.

(1) Indication for identification: ADLib #7

(2) Deposit number: NITE P-939

(3) Date of deposition: Apr. 21, 2010

(4) Depository institution: NITE Patent Microorganisms Depositary (NPMD), Incorporated Administrative Agency National Institute of Technology and Evaluation

2.

(1) Indication for identification: ADLib #15

(2) Deposit number: NITE P-940

(3) Date of deposition: Apr. 21, 2010

(4) Depository institution: NITE Patent Microorganisms Depositary (NPMD), Incorporated Administrative Agency National Institute of Technology and Evaluation

[Sequence Listing Free Text]

SEQ ID NO: 1

<223> anti-LPG antibody #15 light chain variable region CDR1

SEQ ID NO: 2

<223> anti-LPG antibody #15 light chain variable region CDR2

SEQ ID NO: 3

<223> anti-LPG antibody #15 light chain variable region CDR3

SEQ ID NO: 4

<223> anti-LPG antibody #15 heavy chain variable region CDR1

SEQ ID NO: 5

<223> anti-LPG antibody #15 heavy chain variable region CDR2

SEQ ID NO: 6

<223> anti-LPG antibody #15 heavy chain variable region CDR3

SEQ ID NO: 7

<223> anti-LPG antibody #15 light chain variable region

SEQ ID NO: 8

<223> anti-LPG antibody #15 heavy chain variable region

SEQ ID NO: 9

<223> anti-LPG antibody #15 light chain variable region cDNA
SEQ ID NO: 10
<223> anti-LPG antibody #15 heavy chain variable region cDNA
SEQ ID NO: 11
<223> anti-LPG antibody #7 light chain variable region CDR1
SEQ ID NO: 12
<223> anti-LPG antibody #7 light chain variable region CDR2
SEQ ID NO: 13
<223> anti-LPG antibody #7 light chain variable region CDR3
SEQ ID NO: 14
<223> anti-LPG antibody #7 heavy chain variable region CDR1
SEQ ID NO: 15
<223> anti-LPG antibody #7 heavy chain variable region CDR2
SEQ ID NO: 16
<223> anti-LPG antibody #7 heavy chain variable region CDR3
SEQ ID NO: 17
<223> anti-LPG antibody #7 light chain variable region
SEQ ID NO: 18
223> anti-LPG antibody #7 heavy chain variable region
SEQ ID NO: 19
<223> anti-LPG antibody #7 light chain variable region cDNA
SEQ ID NO: 20
<223> anti-LPG antibody #7 heavy chain variable region cDNA

---

The invention claimed is:

1. An antibody comprising: a light chain variable region comprising the complementarity determining regions (CDRs) having the amino acid sequences of SEQ ID NOs: 1 to 3; and a heavy chain variable region comprising the complementarity determining regions (CDRs) having the amino acid sequences of SEQ ID NOs: 4 to 6.

2. An antibody comprising: a light chain variable region comprising the amino acid sequence of SEQ ID NO: 7 or the amino acid sequence of SEQ ID NO: 7 in which one to 10 amino acids in the framework region are substituted, deleted, added, and/or inserted; and a heavy chain variable region comprising the amino acid sequence of SEQ ID NO: 8 or the amino acid sequence of SEQ ID NO: 8 in which one to 10 amino acids in the framework region are substituted, deleted, added, and/or inserted.

3. An antibody comprising: a light chain variable region comprising the complementarity determining regions (CDRs) having the amino acid sequences of SEQ ID NOs: 11 to 13; and a heavy chain variable region comprising the complementarity determining regions (CDRs) having the amino acid sequences of SEQ ID NOs: 14 to 16.

4. An antibody comprising: a light chain variable region comprising the amino acid sequence of SEQ ID NO: 17 or the amino acid sequence of SEQ ID NO: 17 in which one to 10 amino acids in the framework region are substituted, deleted, added, and/or inserted; and a heavy chain variable region comprising the amino acid sequence of SEQ ID NO: 18 or the amino acid sequence of SEQ ID NO: 18 in which one to 10 amino acids are substituted, deleted, added, and/or inserted.

5. A composition for suppressing a repellent effect of lysophosphatidylglucoside on axon extension of a neuron expressing TrkA, the composition comprising the antibody of claim 1, 2, 3 or 4 as an active ingredient.

6. The composition of claim 5, which is a pharmaceutical composition.

7. A method for extending an axon of a neuron expressing TrkA, the method comprising administering the antibody of claim 1, 2, 3 or 4 to a subject in need thereof to suppress a repellent effect of lysophosphatidylglucoside.

* * * * *